US009820808B2

United States Patent
Lefler et al.

(10) Patent No.: US 9,820,808 B2
(45) Date of Patent: *Nov. 21, 2017

(54) METHOD FOR TREATING THE THORACIC REGION OF A PATIENT'S BODY

(71) Applicant: Avent, Inc., Alpharetta, GA (US)

(72) Inventors: Amy Lefler, Mono (CA); Neil Godara, Milton (CA); Robert Harrison, Milton (CA)

(73) Assignee: Avent, Inc., Alpharetta, GA (US)

( * ) Notice: Subject to any disclaimer, the term of this patent is extended or adjusted under 35 U.S.C. 154(b) by 125 days.

This patent is subject to a terminal disclaimer.

(21) Appl. No.: 15/178,692

(22) Filed: Jun. 10, 2016

(65) Prior Publication Data

US 2016/0278846 A1  Sep. 29, 2016

Related U.S. Application Data

(60) Division of application No. 12/199,572, filed on Aug. 27, 2008, now Pat. No. 9,364,281, which is a
(Continued)

(51) Int. Cl.
*A61B 18/14* (2006.01)
*A61B 18/00* (2006.01)
*A61B 90/00* (2016.01)

(52) U.S. Cl.
CPC ........ *A61B 18/148* (2013.01); *A61B 18/1482* (2013.01); *A61B 2018/00023* (2013.01); *A61B 2018/0044* (2013.01); *A61B 2018/00083* (2013.01); *A61B 2018/00196* (2013.01); *A61B 2018/00434* (2013.01); *A61B 2018/00791* (2013.01); *A61B 2018/00815* (2013.01);
(Continued)

(58) Field of Classification Search
CPC ........ A61B 2018/0044; A61B 18/1482; A61B 18/1487; A61B 2018/00023; A61B 2018/00083; A61B 2018/00196; A61B 2018/00434; A61B 2018/00791; A61B 2018/1497; A61B 2090/064
USPC ................. 128/898; 606/20–49; 607/88–104
See application file for complete search history.

(56) References Cited

U.S. PATENT DOCUMENTS 4,041,931 A   8/1977  Elliott et al.
4,202,349 A   5/1980  Jones
(Continued)

FOREIGN PATENT DOCUMENTS

CA   1 160 932 A   1/1984
EP   0 547 772 A   6/1993
(Continued)

OTHER PUBLICATIONS

International Search Report (PCT/CA2006/001163)—7 pages.
(Continued)

*Primary Examiner* — William Thomson
*Assistant Examiner* — Scott T. Luan
(74) *Attorney, Agent, or Firm* — Dority & Manning, P.A.

(57) ABSTRACT

A method is disclosed for the treatment of a thoracic region of a patient's body. Embodiments of the method comprise positioning an energy delivery portion of an electrosurgical device to face a segment of a thoracic vertebra at a distance from the segment; and cooling the energy delivery portion and delivering energy through the energy delivery portion.

9 Claims, 20 Drawing Sheets

Related U.S. Application Data continuation-in-part of application No. 12/176,035, filed on Jul. 18, 2008, now abandoned, which is a continuation-in-part of application No. 11/457,697, filed on Jul. 14, 2006, which is a continuation-in-part of application No. 11/105,527, filed on Apr. 14, 2005, now Pat. No. 8,882,755, and a continuation-in-part of application No. 11/105,490, filed on Apr. 14, 2005, now abandoned, and a continuation-in-part of application No. 11/105,524, filed on Apr. 14, 2005, now Pat. No. 7,294,127, said application No. 11/105,527 is a continuation-in-part of application No. 10/087,856, filed on Mar. 5, 2002, now Pat. No. 6,896,675, said application No. 11/105,490 is a continuation-in-part of application No. 10/087,856, filed on Mar. 5, 2002, now Pat. No. 6,896,675, said application No. 11/105,524 is a continuation-in-part of application No. 10/087,856, filed on Mar. 5, 2002, now Pat. No. 6,896,675, said application No. 11/457,697 is a continuation-in-part of application No. 11/381,783, filed on May 5, 2006, now abandoned, and a continuation-in-part of application No. 10/864,410, filed on Jun. 10, 2004, now Pat. No. 7,163,536, and a continuation-in-part of application No. 11/207,707, filed on Aug. 22, 2005, now abandoned, which is a continuation-in-part of application No. 11/079,318, filed on Mar. 15, 2005, now Pat. No. 7,593,778, which is a continuation-in-part of application No. 10/382,836, filed on Mar. 7, 2003, now abandoned, said application No. 11/207,707 is a continuation-in-part of application No. 11/125,247, filed on May 10, 2005, now Pat. No. 7,306,596, which is a continuation-in-part of application No. 10/853,126, filed on May 26, 2004, now abandoned.

(60) Provisional application No. 60/950,706, filed on Jul. 19, 2007, provisional application No. 60/604,348, filed on Aug. 25, 2004, provisional application No. 60/743,511, filed on Mar. 16, 2006, provisional application No. 60/595,559, filed on Jul. 14, 2005, provisional application No. 60/595,560, filed on Jul. 14, 2005, provisional application No. 60/744,518, filed on Apr. 10, 2006.

(52) U.S. Cl.
CPC ........... *A61B 2018/00821* (2013.01); *A61B 2018/1497* (2013.01); *A61B 2090/064* (2016.02); *A61B 2218/002* (2013.01); *A61B 2218/007* (2013.01)

(56) References Cited

U.S. PATENT DOCUMENTS

| | | |
|---|---|---|
| 4,257,429 A | 3/1981 | Dickhudt et al. |
| 4,419,095 A | 12/1983 | Nebergall et al. |
| 4,447,239 A | 5/1984 | Krutten |
| 4,548,207 A | 10/1985 | Reimels |
| 4,612,934 A | 9/1986 | Borkan |
| 4,657,024 A | 4/1987 | Coneys |
| 5,191,900 A | 3/1993 | Mishra |
| 5,209,749 A | 5/1993 | Buelna |
| 5,342,343 A | 8/1994 | Kitaoka et al. |
| 5,342,357 A | 8/1994 | Nardella |
| 5,397,338 A | 3/1995 | Grey et al. |
| 5,429,597 A | 7/1995 | DeMello et al. |
| 5,429,617 A | 7/1995 | Hammersmark et al. |
| 5,433,739 A * | 7/1995 | Sluijter ............ A61B 18/1482 607/113 |
| 5,545,193 A | 8/1996 | Fleischman et al. |
| 5,571,147 A | 11/1996 | Sluijter et al. |
| 5,693,043 A | 12/1997 | Kittrell et al. |
| 5,759,174 A | 6/1998 | Fischell et al. |
| 5,766,171 A | 6/1998 | Silvestrini |
| 5,776,092 A | 7/1998 | Farin et al. |
| 5,779,642 A | 7/1998 | Nightingale |
| 5,800,428 A | 9/1998 | Nelson et al. |
| 5,855,577 A | 1/1999 | Murphy-Chutorian et al. |
| 5,895,386 A | 4/1999 | Odell |
| 5,951,546 A | 9/1999 | Lorentzen |
| 6,002,964 A | 12/1999 | Feler et al. |
| 6,056,743 A | 5/2000 | Ellis et al. |
| 6,102,886 A | 8/2000 | Lundquist et al. |
| 6,104,957 A | 8/2000 | Alo et al. |
| 6,126,654 A | 10/2000 | Giba et al. |
| 6,129,726 A | 10/2000 | Edwards |
| 6,146,380 A | 11/2000 | Racz et al. |
| 6,176,857 B1 | 1/2001 | Ashley |
| 6,235,000 B1 | 5/2001 | Milo et al. |
| 6,251,104 B1 | 6/2001 | Kesten et al. |
| 6,277,112 B1 | 8/2001 | Underwood et al. |
| 6,280,441 B1 | 8/2001 | Ryan |
| 6,306,132 B1 | 10/2001 | Moorman et al. |
| 6,315,790 B1 | 11/2001 | Gerberding et al. |
| 6,355,033 B1 | 3/2002 | Moorman et al. |
| 6,379,349 B1 | 4/2002 | Müller et al. |
| 6,464,723 B1 | 10/2002 | Callol |
| 6,471,700 B1 | 10/2002 | Burbank et al. |
| 6,478,783 B1 | 11/2002 | Moorehead |
| 6,501,992 B1 | 12/2002 | Belden et al. |
| 6,562,033 B2 | 5/2003 | Shah et al. |
| 6,582,426 B2 | 6/2003 | Moorman et al. |
| 6,620,156 B1 | 9/2003 | Garito et al. |
| 6,622,731 B2 | 9/2003 | Daniel et al. |
| 6,726,684 B1 | 4/2004 | Woloszko et al. |
| 6,735,474 B1 | 5/2004 | Loeb et al. |
| 6,757,565 B2 | 6/2004 | Sharkey |
| 6,770,070 B1 | 8/2004 | Balbierz |
| 6,773,446 B1 | 8/2004 | Dwyer et al. |
| 6,780,181 B2 | 8/2004 | Kroll et al. |
| 6,847,849 B2 | 1/2005 | Mamo et al. |
| 6,893,421 B1 | 5/2005 | Larsen et al. |
| 6,902,526 B2 | 6/2005 | Katzman |
| 6,932,811 B2 | 8/2005 | Hooven |
| 6,966,902 B2 | 11/2005 | Tsugita et al. |
| 6,974,454 B2 | 12/2005 | Hooven |
| 7,097,641 B1 | 8/2006 | Arless et al. |
| 7,175,631 B2 | 2/2007 | Wilson et al. |
| 7,462,178 B2 | 12/2008 | Woloszko et al. |
| 2001/0000041 A1 | 3/2001 | Selmon et al. |
| 2001/0027309 A1 | 10/2001 | Elsberry |
| 2001/0032001 A1 * | 10/2001 | Ricart ............ A61B 18/1402 607/99 |
| 2001/0056280 A1 | 12/2001 | Underwood |
| 2002/0016588 A1 * | 2/2002 | Wong ............ A61B 18/14 606/32 |
| 2002/0026127 A1 | 2/2002 | Balbierz |
| 2002/0032440 A1 | 3/2002 | Hooven |
| 2002/0049437 A1 | 4/2002 | Silvestrini |
| 2002/0072739 A1 | 6/2002 | Lee |
| 2002/0091384 A1 | 7/2002 | Godinho de Queiroz e Melo |
| 2002/0103484 A1 | 8/2002 | Hooven |
| 2002/0120260 A1 | 8/2002 | Morris et al. |
| 2002/0147485 A1 | 10/2002 | Mamo et al. |
| 2002/0188292 A1 | 12/2002 | Sharkey et al. |
| 2002/0193781 A1 | 12/2002 | Loeb |
| 2003/0014047 A1 | 1/2003 | Woloszko et al. |
| 2003/0015707 A1 | 1/2003 | Bosco et al. |
| 2003/0023239 A1 | 1/2003 | Burbank et al. |
| 2003/0032936 A1 | 2/2003 | Lederman |
| 2003/0040742 A1 | 2/2003 | Underwood |
| 2003/0093007 A1 | 5/2003 | Wood |
| 2003/0100895 A1 | 5/2003 | Simpson et al. |
| 2003/0109870 A1 | 6/2003 | Lee |
| 2003/0125729 A1 | 7/2003 | Hooven et al. |
| 2003/0153906 A1 | 8/2003 | Sharkey |
| 2003/0158545 A1 | 8/2003 | Hovda et al. |
| 2003/0212394 A1 | 11/2003 | Pearson et al. |

(56) References Cited

U.S. PATENT DOCUMENTS

| | | |
|---|---|---|
| 2003/0212395 A1 | 11/2003 | Woloszko |
| 2003/0233125 A1 | 12/2003 | Kaplan et al. |
| 2004/0054366 A1 | 3/2004 | Davison et al. |
| 2004/0082942 A1 | 4/2004 | Katzman |
| 2004/0106891 A1 | 6/2004 | Langan et al. |
| 2004/0187875 A1 | 9/2004 | He et al. |
| 2004/0199161 A1 | 10/2004 | Truckai et al. |
| 2004/0215287 A1 | 10/2004 | Swoyer et al. |
| 2004/0249373 A1 | 12/2004 | Gronemeyer et al. |
| 2004/0267203 A1 | 12/2004 | Potter et al. |
| 2004/0267254 A1 | 12/2004 | Manzo |
| 2005/0033372 A1 | 2/2005 | Gerber et al. |
| 2005/0049570 A1 | 3/2005 | Chin et al. |
| 2005/0085806 A1 | 4/2005 | Auge, II et al. |
| 2005/0096718 A1 | 5/2005 | Gerber et al. |
| 2005/0177209 A1 | 8/2005 | Leung et al. |
| 2005/0177211 A1 | 8/2005 | Leung et al. |
| 2005/0187542 A1 | 8/2005 | Auge |
| 2005/0240238 A1 | 10/2005 | Mamo |
| 2006/0020297 A1 | 1/2006 | Gerber et al. |
| 2006/0025763 A1 | 2/2006 | Nelson et al. |
| 2009/0024124 A1 | 1/2009 | Lefler et al. |

FOREIGN PATENT DOCUMENTS

| | | |
|---|---|---|
| EP | 0 642 800 A1 | 3/1995 |
| EP | 0 865 768 A1 | 9/1998 |
| EP | 0 651 661 B1 | 6/2000 |
| EP | 1 344 497 A1 | 9/2003 |
| WO | WO 81/03272 A1 | 11/1981 |
| WO | WO 94/02077 A2 | 2/1994 |
| WO | WO 94/09560 A1 | 4/1994 |
| WO | WO 94/22384 A1 | 10/1994 |
| WO | WO 94/24948 A1 | 11/1994 |
| WO | WO 95/10318 A1 | 4/1995 |
| WO | WO 95/10320 A1 | 4/1995 |
| WO | WO 95/10327 A1 | 4/1995 |
| WO | WO 95/21578 A1 | 8/1995 |
| WO | WO 96/39967 A1 | 12/1996 |
| WO | WO 97/06739 A2 | 2/1997 |
| WO | WO 97/06855 | 2/1997 |
| WO | WO 97/24074 | 7/1997 |
| WO | WO 98/19613 | 5/1998 |
| WO | WO 98/27879 | 7/1998 |
| WO | WO 98/31290 | 7/1998 |
| WO | WO 98/58747 | 12/1998 |
| WO | WO 99/42037 | 8/1999 |
| WO | WO 99/43263 | 9/1999 |
| WO | WO 99/48548 | 9/1999 |
| WO | WO 01/45579 A1 | 6/2001 |
| WO | WO 01/67975 A2 | 9/2001 |
| WO | WO 01/70114 A1 | 9/2001 |
| WO | WO 01/74251 A2 | 10/2001 |
| WO | WO 01/80724 A2 | 11/2001 |
| WO | WO 02/45609 A1 | 6/2002 |
| WO | WO 03/037162 A2 | 5/2003 |
| WO | WO 03/065917 A1 | 8/2003 |
| WO | WO 03/103522 A1 | 12/2003 |

OTHER PUBLICATIONS

International Search Report (PCT/CA2006/000229)—4 pages.
Buijs et al., "Radiofrequency Treatment of Sacroiliac Joint-Related Pain Aimed at the First Three Sacral Dorsal Raml: A Minimal Approach", Pain Clinic, 16(2):139-146, 2004.
Jiang et al., "Comparison Between Radiofrequency Coagulation Plus Small Needle Knife and Single Method in Treatment of Sacrolumbar Pain", Chinese Journal of Clinical Rehabilitation, 7(20):2844-2845, 2003.
Plancarte et al., "Radiofrequency Procedures for Sacral and Pelvic Region Pain", Pain Pratice 2(3):248-249, 2002.
Fukui et al., "Successful Relief of Hip Joint Pain by Percutaneous Radiofrequency Nerve Thermocoagulation in a Patient with Contraindictions for Hip Arthroplasty", J. Anesth., 15(3):173-175, 2001.
Cohen et al., "Pulsed Radiofrequency as a Treatment for Groin Pain and Orchialgia", Urology, 61(3):645, 2003.
Kawaguchi et al., "Percutaneous Radiofrequency Lesioning of Sensory Branches of the Obturator and Femoral Nerves for the Treatment of Hip Joint Pain", Reg Anesth Pain Med. 26(6):578-581, 2001.
Akatov et al., "Percutaneous Radiofrequency Destruction of the Obturator Nerve for Treatment of Pain Caused by Coxarthrosis", Stereotact Funct Neurosurg. 61(1-4 Pt 2):278-280, 1997.
Ferrante et al., "Radiofrequency Sacroiliac Joint Denervation for Sacroiliac Syndrome", Reg Anesth Pain Med 26(2):137-142, 2001.
Gopalani et al., "A Novel Technique for Treating Nonsurgical Hip Pain with Radiofrequency Lesioning of the Sensory Branches of the Obturator and Femoral Nerves: A Case Report", Archives of Physical Medicine and Rehabilitation, 84(9):E23, 2003.
Pino et al., "Morphologic Analysis of Bipolar Radiofrequency Lesions: Implications for Treatment of the Sacroiliac Joint", Reg Anesth Pain Med. 30(4):335-338, 2005.
Yin et al., "Sensory Stimulation-Guided Sacroiliac Joint Radiofrequency Neurotomy: Technique Based on Neuroanatomy of the Dorsal Sacral Plexus", Spine, 28(20):2419-2425, 2003.
Ahadian, "Pulsed Radiofrequency Neruotomy: Advances in Pain Medicine", Curr Pain Headache Rep, 8(1):34-40, 2004.
Gevargez et al., "CT-Guided Percutaneous Radiofrequency Denervation of the Sacroiliac Joint", Eur Radiol, 12(6):1360-1365, 2002.
Anis et al., "Use of Radio-Frequency Ablation for the Palliative Treatment of Sacral Chordoma", AJNR, 25(9):1589-1591, 2004.
Conaghan et al., "Sacral Nerve Stimulation can be Successful in Patients with Ultrasound Evidence of External Anal Sphincter Disruption", Diseases of the Colon and Rectum, 48(8):1610-1614, 2005.
Kirsch et al., "Proton Radiotherapy for Hodgkin's Disease in the Sacrum", Lancet Oncology, 6(7):532:533, 2005.
Leng et al., "How Sacral Nerve Stimulation Neuromodulation Works", Urol Clin North Am., 32(1):11-18, 2005.
Kirkham et al., "Neuromodulation Through Sacral Nerve Roots 2 to 4 with a Finetech-Brindley Sacral Posterior and Anterior Root Stimulator", Spinal Cord, 40(6):272-281, 2002.
Simon, "Sacroiliac Joint Injection and Low Back Pain", Interventional Pain Management, 535-539, 2001.
Kline et al., "Radiofrequency Techniques in Clincal Practice", Interventional Pain Management 243-290, 2001.
Cole et al., "The Sacroiliac Joint: A Functional Approach", Critical Reviews in Physical and Rehabilitation Medicine, 8(1&2):125-152, 1996.
Atlihan et al., "Anatomy of the Anterior Sacroiliac Joint with Reference to Lumbosacral Nerves", Clinical Orthopaedics and Related Research, 376:2360241, 2000.
Calvillo et al., "Anatomy and Pathophysiology of the Sacroiliac Joint", Current Review of Pain, 4:356-261, 2000.
Davies et al., "Radiofrequency Treatment in the United States", Pain Practice 2(3):192-194, 2000.
Ebraheim et al., "Anatomic Considerations for Posterior Approach to the Sacroiliac Joint", Spine, 21(23):2709-2712, 1996.
Fortin et al., "Three Pathways Between the Sacroiliac Joint and Neural Structures", Am J Neuroradiol., 20:1429-1434, 1999.
Fortin et al., "Sacroiliac Joint Innervation and Pain", The American Journal of Orthopedics, 28:68-90, 1999.
Liguoro et al., "The Posterior Sacral Foramina: An Anatomical Study", J. Anat, 195:301-304, 1999.
Murata et al., "Origins and Pathway of Sensory Nerve Fibers to the Ventral and Dorsal Sides of the Sacroiliac Joint in Rats", Journal of Orthopaedic Research, 19:379-383, 2001.
Prithvi et al., "The Current Status of the Practice of Radiofrequency in the World", Pain Practice, 2(3):176-179, 2002.
Slipman et al., "Sacroiliac Joint Syndrome", Pain Physician, 4(2):143-152, 2001.

(56) References Cited

OTHER PUBLICATIONS

Van Zundert et al., "Application of Radiofrequency Treatment in Practical Pain Management: State of the Art", Pain Practice, 2(3):269-278, 2002.

Dreyfuss et al., "Lumbar Radiofrequency Neurotomy for Chronic Zygapophyseal Joint Pain: A Pilot Study Using Dual Medial Branch Blocks", ISIS Scientific Newsletter 3(2):13-30, 1999.

Deer, "Injections for the Diagnosis and Treatment of Spinal Pain", American Society of Anesthesiologists 32(Chapter 6):52-69, 2004.

Cohen et al., "Lateral Branch Blocks as a Treatment of Sacroiliac Joint Pain: A Pilot Study", Regional Anesthesia Pain Medicine, 28(2):113-119, 2003.

Bogduk et al., "Technical Limitations to the Efficacy of Radiofrequency Neurotomy for Spinal Pain", Neurosurgery 20(4):529-535, 1987.

Lord et al., "Percutaneous Radiofrequency Neurotomy in the Treatment of Cervical Zygapophyseal Joint Pain: A Caution", Neurosurgery 36(4):732-739, 1995.

Lau et al., "The Surgical Anatomy of Lumbar Medial Branch Neurotomy (Facet Denervation)", Pain Medicine 5(3):289-298, 2004.

Lord et al., "Percutaneous Radio-Frequency Neurotomy for Chronic Cervical Zygapophyseal-Joint Pain", New England Journal of Medicine 335(23):1721-1726, 1996.

Hooten et al., "Radiofrequency Neurotomy for Low Back Pain: Evidence-Based Procedural Guidelines", Pain Medicine 6(2):129-138, 2005.

Dreyfuss et al., "Radiofrequency Neurotomy of the Zygapophyseal and Sacroiliac Joints", Pain Proc, 2(Chapter 32): 395-420, 2000.

Baylis Medical Company, Inc., "Technology Notes—RF Lesion Size in Relation to Cannula Gauge", 2005.

Baylis Medical Company, Inc., "Baylis Medical Company—Radiopaque Cannula", 2005.

Curatolo et al., "Re: Niemisto L., Kalso E., Malmivaara A., et al. Radiofrequency Denervation for Neck and Back Pain: A Systematic Review Within the Framework of the Cochrane Collaboration Back Review Group. Spine 2003, 28:1877-88", Spine 30(2):263-268, 2005.

Cohen, "Sacroiliac Joint Pain: A Comprehensive Review of Anatomy, Diagnosis, and Treatment", Anesth Analg 101:1440-1453, 2005.

Valleylab—RF Pain Management System, Sep. 16, 2004, http://www.valleylab.com/static/pain/products-generator.html.

\* cited by examiner

METHOD FOR TREATING THE THORACIC REGION OF A PATIENT'S BODY

CROSS REFERENCES TO RELATED APPLICATIONS

The present application is a divisional of U.S. patent application Ser. No. 12/199,572 (filed Aug. 27, 2008), which is a continuation-in-part of U.S. patent application Ser. No. 12/176,035 (filed Jul. 18, 2008), which claims the benefit of U.S. Provisional Patent Application No. 60/950,706 (filed Jul. 19, 2007) and is a continuation-in-part of U.S. patent application Ser. No. 11/457,697 (filed Jul. 14, 2006). U.S. patent application Ser. No. 11/457,697 (filed Jul. 14, 2006) is a continuation-in-part of U.S. patent application Ser. No. 11/105,527 (filed Apr. 14, 2005), now U.S. Pat. No. 8,882,755, Ser. No. 11/105,490 (filed Apr. 14, 2005), and Ser. No. 11/105,524 (filed Apr. 14, 2005), all of which claim the benefit of U.S. Provisional Patent Application 60/604,348 (filed on Aug. 25, 2004), and are continuations-in-part of U.S. patent application Ser. No. 10/087,856 (filed on Mar. 5, 2002), now U.S. Pat. No. 6,896,675. This application is also a continuation-in-part of U.S. patent application Ser. No. 11/381,783 (filed on May 5, 2006). This application is also a continuation-in-part of U.S. patent application Ser. No. 10/864,410 (filed on Jun. 10, 2004). This application is also a continuation-in-part of U.S. patent application Ser. No. 11/207,707 (filed on Aug. 22, 2005). U.S. patent application Ser. No. 11/207,707 is a continuation-in-part of U.S. patent application Ser. No. 11/079,318 (filed on Mar. 15, 2005), now U.S. Pat. No. 7,593,778, which is a continuation-in-part of U.S. patent application Ser. No. 10/382,836 (filed on Mar. 7, 2003). U.S. patent application Ser. No. 11/207,707 is also a continuation-in-part of U.S. patent application Ser. No. 11/125,247 (filed on May 10, 2005), which is a continuation-in-part of U.S. patent application Ser. No. 10/853,126 (filed on May 26, 2004). This application also claims the benefit of U.S. Provisional Patent Applications 60/743,511 (filed on Mar. 16, 2006), 60/595,559 (filed on Jul. 14, 2005), 60/595,560 (filed on Jul. 14, 2005), and 60/744,518 (filed on Apr. 10, 2006). All of the aforementioned patents and applications are incorporated herein by reference in their entirety.

TECHNICAL FIELD

The invention relates to a method of electrosurgery. Specifically, the invention relates to a method of electrosurgery for treating a thoracic region of a spine of a patient's body.

BACKGROUND OF THE INVENTION

Radiofrequency energy is used in order to treat pain radiating from nerves in the spine. Several prior-art approaches exist in order to target an RF probe at the desired target location. However, regardless of the approach used, a limitation of RF techniques is that the lesion forms immediately adjacent to the probe tip. Hence the efficacy of the treatment is dependent upon the probe tip being in contact with or in close proximity to the target nerve. The treatment may be ineffective if the probe is positioned in the general area of the target nerve but not adjacent to the nerve. This has been outlined in Bogduk et al. (Neurosurgery, 20(4): 529-535, 1987) as the reason for low success rate of RF neurotomy in the spine, "despite the accurate placement of electrodes onto anatomically correct target points, the lesions may not fully incorporate the nerve. The electrode tip may have rested close to the nerve. However, RF electrodes coagulate circumferentially and only minimally distally, therefore the lesion may have been placed superficial to the nerve." This problem is not limited to a perpendicular approach, as in the parallel approach even though "an electrode lying parallel to the nerve is more likely to incorporate the nerve . . . this modification relies critically on the accurate placement of the electrode". Hence, the success of RF lesioning in the spine is dependent on the accurate positioning of the probe at the target nerve.

The thoracic region of the spine is a stable structure; thus a high prevalence of thoracic pain would not be expected. However, it has been shown that between 15 and 24% of people suffering from spinal pain experience upper back/thoracic pain (Linton et al., 1998; Manchikanti and Pampati, 2002). Facet joint pain accounts for 42% to 48% of patients with chronic thoracic pain (Manchikanti et al., 2004; Manchikanti et al., 2002). In summary, thoracic facet pain represents 6 to 12% of all spinal pain. Thus the present invention is directed to treating pain in the thoracic region of the spine.

SUMMARY

The course of the nerves in the thoracic spine varies considerably between individuals as well as between the different thoracic levels. Thus, in order to create an effective lesion, the electrosurgical device needs to be positioned to suit the varying anatomies. Embodiments of the present invention allow for effective treatment in the different thoracic levels. The use of cooling with standard RF allows the lesion to be formed substantially distal to the tip of the electrosurgical where the lesion forms between the electrosurgical device and the thoracic vertebra. This allows for effective lesioning of the target nerve when the electrosurgical device is positioned at a distance from the nerve. This ensures that when the probe is positioned near the course of the target nerve, the resulting lesion encompasses the target nerve. This provides an advantageous benefit not found in the prior art, in that it obviates the need for a probe to be placed in very close proximity to a target nerve in order to effectively lesion the target nerve. Thus, embodiments of the present invention are directed to a system and method for providing an effective treatment of a target nerve in the spine. More specifically, embodiments of the present invention are directed to treating the thoracic region of the spine.

In one broad aspect embodiments of the present invention are directed to a method of treatment of a thoracic region of a patient's body, the method comprising: positioning an energy delivery portion of an electrosurgical device to face a segment of a thoracic vertebra at a distance from the segment; and cooling the energy delivery portion and delivering energy through the energy delivery portion. As one feature of this aspect a lesion is formed at least substantially distal to the energy delivery portion. As another feature of this aspect a lesion is formed at a location at least between the energy delivery portion and the segment of the thoracic vertebra.

In another broad aspect embodiments of the present invention are directed to a method of treatment of a thoracic region of a patient's body, the method comprising: inserting an introducer apparatus into the patient's body, the apparatus comprising a cannula and an obturator disposed within a lumen of the cannula, the obturator protruding from a distal end of the cannula; positioning the apparatus such that a distal tip of the obturator abuts a segment of a thoracic vertebra; removing the obturator from within the cannula;

inserting an electrosurgical device within the cannula, to position an energy delivery portion of the electrosurgical device at a distance from the segment of the thoracic vertebra; and delivering energy through the energy delivery portion and cooling the energy delivery portion, whereby a lesion forms at least between the energy delivery portion and the segment of the thoracic vertebra.

BRIEF DESCRIPTION OF THE DRAWINGS

In order that the invention may be readily understood, embodiments of the invention are illustrated by way of examples in the accompanying drawings, in which.

DETAILED DESCRIPTION OF THE INVENTION

Figure 1A:
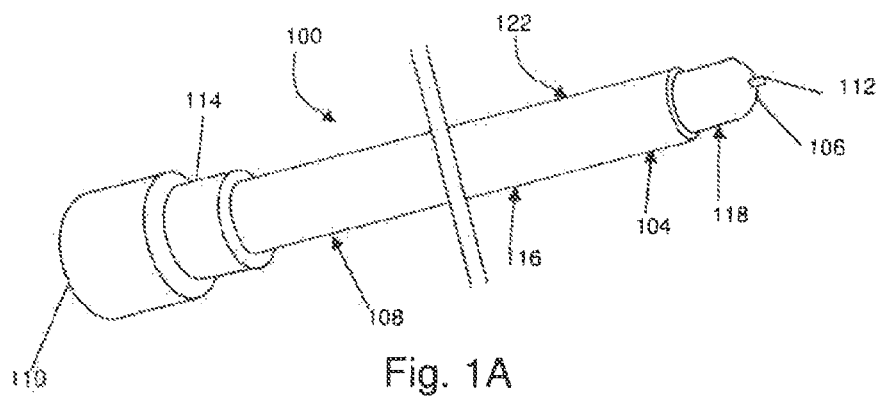
FIG. 1A is a perspective view of an embodiment of an electrosurgical device suitable for use with a method of the present invention.

In one broad aspect, the present invention comprises a method for treating a thoracic region of a spine of a patient's body, for example in order to treat pain. Some embodiments of the method comprise positioning an energy delivery portion of an electrosurgical device to face a segment of a thoracic vertebra at a distance from the segment; and cooling the energy delivery portion and delivering energy through the energy delivery portion. As a feature of this aspect a lesion is formed at least substantially distal to the energy delivery portion. As another feature of this aspect a lesion is formed at a location at least between the energy delivery portion and the segment of the thoracic vertebra. In one feature of this aspect the energy delivery portion electrosurgical device may be inserted and positioned in a relatively safe, effective, and efficient manner. In one example, the energy delivery portion is positioned in proximity to a medial branch of a thoracic dorsal ramus nerve and a lesion is formed at the medial branch of the dorsal ramus nerve. In some embodiments the lesion may form between the energy delivery device and a segment of the thoracic vertebra.

In another broad aspect, the embodiments of the present invention are directed to a method of treatment of the thoracic region of a patient's body. Some embodiments of the method comprise inserting an introducer apparatus into the patient's body. The apparatus comprises a cannula and an obturator disposed within a lumen of the cannula such the obturator protrudes from a distal end of the cannula; positioning the apparatus such that a distal tip of the obturator abuts a segment of the thoracic vertebra; and inserting an electrosurgical device within the cannula such that an energy delivery portion of the device is positioned at a distance from the segment of the thoracic vertebra. The method further comprises delivering energy through the energy delivery portion and cooling the energy delivery portion such that a lesion forms at least between the energy delivery portion and the segment of the thoracic vertebra.

In another embodiment, a finder needle may be placed at the superior-lateral aspect to guide the placement of the introducer apparatus.

In some embodiments the electrosurgical device is positioned at a superolateral aspect of a transverse process of a thoracic vertebra. In some such embodiments, the electrosurgical device is inserted into the patient's body such that at least a portion of the electrosurgical device is generally upstanding relative to a portion of the superolateral aspect. In some such embodiments, inserting the electrosurgical device comprises aligning the electrosurgical device such that it is oriented substantially away from an anterior-posterior axis of the patient's body, in a substantially cranial direction and advancing the electrosurgical device into the patient's body towards the superior aspect of the transverse process. In one example of the embodiment, the electrosurgical device is positioned at a distance from the superior-lateral aspect. In one example the device is positioned such that an energy delivery portion of the device is facing the superior-lateral aspect of the transverse process. In some embodiments the lesion forms substantially distal to the energy delivery portion of the device.

In alternate embodiments, the electrosurgical device is inserted into the patient's body such that at least a portion of the electrosurgical device is positioned at a centroid of the transverse process. In some such embodiments, inserting the electrosurgical device comprises aligning an electrosurgical device substantially with an anterior-posterior axis of a patient's body; advancing the electrosurgical device into the patient's body towards the centroid of the transverse process; and positioning the energy delivery portion in proximity to the superolateral aspect of the transverse process. In one example of this embodiment the electrosurgical device is positioned at a distance from the superolateral aspect. In one example, the lesion forms at least substantially distal to the energy delivery portion of the device. In an example of this embodiment a lesion is formed between the energy delivery portion and the superior-lateral aspect.

In further embodiments, the target site is a lamina of the thoracic vertebra. In some such embodiments, the electrosurgical device is inserted into the patient's body such that at least a portion of the electrosurgical device is generally upstanding relative to a portion of the lamina. In some such embodiments, inserting the electrosurgical device comprises aligning the electrosurgical device such that it is oriented substantially away from an anterior-posterior axis of the patient's body, in a substantially lateral direction and advancing the electrosurgical device into the patient's body towards the lamina. Further embodiments of the present invention are described herein below:

With specific reference now to the drawings in detail, it is stressed that the particulars shown are by way of example and for purposes of illustrative discussion of certain embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Device

Several embodiments of electrosurgical devices suitable for use with embodiments of the present invention are disclosed in U.S. patent application Ser. No. 11/457,697 (filed on Jul. 14, 2006), which is incorporated herein by reference. One particular embodiment of an electrosurgical device suitable for use with embodiments of the present invention will presently be described. With reference first to FIG. 1A, an embodiment of a device suitable for use with embodiments of the present invention is probe 100. Probe 100 is an elongate member, comprising a shaft 122, a distal region 104, a distal end 106, a proximal region 108, and a proximal end 110. As used herein, the terms "distal" and "proximal" are defined with respect to the user and when the device is in use. That is, the term "distal" refers to the part or portion further away from the user, while the term "proximal" refers to the part or portion closer to the user, when the device is in use.

Probe 100 defines a lumen 124. Proximal end 110 defines an aperture, which is in communication with lumen 124. Probe 100 comprises an electrically insulated portion 116 and an electrically exposed conductive portion 118. Electrically exposed conductive portion 118 may also be referred to as an active electrode and is an example of an "energy delivery portion" mentioned herein.

The proximal region of probe 100 comprises a hub 114. Hub 114 is structured to operatively connect other devices, such as connector cables, cannulae, tubes, or other hubs, for example, to probe 100. For example, probe 100 may be coupled to an energy source and/or to a source of cooling via respective connecting means (for example, an electrical cable and/or flexible tubing) which may be associated with hub 114. Hub 114 may also serve as a handle or grip for probe 100. Hub 114 may be manufactured from a number of different materials, including, but not limited to, plastics, polymers, metals, or combinations thereof. Furthermore, hub 114 may be attached to probe 100 by a number of different means. For example, in one embodiment, hub 114 may be made from polypropylene, and may be attached to probe 100 by insert molding.

The size of probe 100 may vary, depending upon which of the method embodiments, described herein below, are used. In some embodiments, the length from distal end 106 to proximal end 110 of probe 100 may be between about 5 cm and about 40 cm and the outer diameter of shaft 122 may be between about 0.65 mm and about 2.00 mm (between about 20 G and about 12 G). In one specific example, the length of the probe may be about 7.5 cm and the outer diameter may be about 1.5 mm. Furthermore, the size and shape of active electrode 118 may vary, as is further described in U.S. patent application Ser. No. 11/457,697, previously incorporated herein by reference. For example, in some embodiments, active electrode 118 may be between about 2 mm and about 8 mm in length. In other embodiments, active electrode 118 may comprise substantially only the distal face of probe 100.

In some embodiments, electrically insulated portion 116 may be formed by coating a portion of shaft 122 with an electrically insulative coating, covering, or sheathing. For example, in one particular embodiment, shaft 122 of probe 100 may be fabricated from a biocompatible metal or alloy, for example stainless steel, which may be overlaid in part by an insulating coating, for example polytetrafluoroethylene (PTFE). In other embodiments, shaft 122 may be fabricated from another metal, such as nitinol or titanium, and/or the insulating coating may comprise a different electrically insulating material, including but not limited to polyethylene terephthalate (PET). In other embodiments, other metals or electrically insulating materials may be used.

Probe 100 is structured such that it may be cooled by the internal circulation of a cooling fluid. Such a configuration, whereby a cooling medium does not exit from a distal region 104 of probe 100, may be referred to as an internally-cooled probe. The cooling fluid may be any fluid suitable for removing heat from probe 100 during surgery, for example water. Other examples of cooling fluid include, but are not limited to, liquid nitrogen and saline. Furthermore, the fluid may be at any temperature suitable for removing heat from the probe during surgery, for example between about 0° C. and about 25° C. More specifically, the temperature of the fluid may be at about room temperature (21° C.), about 4° C., or about 0° C., depending on the application.

The fluid may be delivered or circulated at a wide range of flow-rates. An appropriate flow-rate may be determined or calculated based on a number of factors, including the conductivity and heat capacity of probe 100, the cooling fluid and/or the tissue, and the desired temperature of distal end 106 of probe 100, among other factors. In some embodiments, the fluid may be delivered at between about 10 ml/min and about 30 ml/min.

Figure 1B:
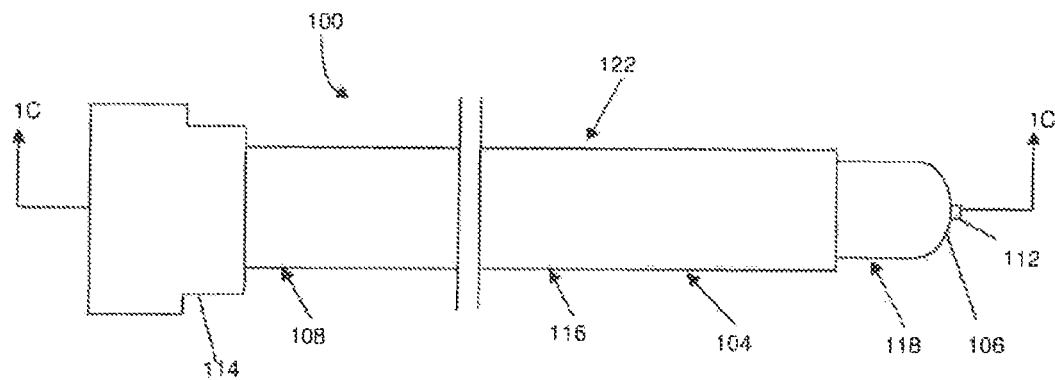
FIG. 1B is a top view of the device of FIG. 1A.
Figure 1C:
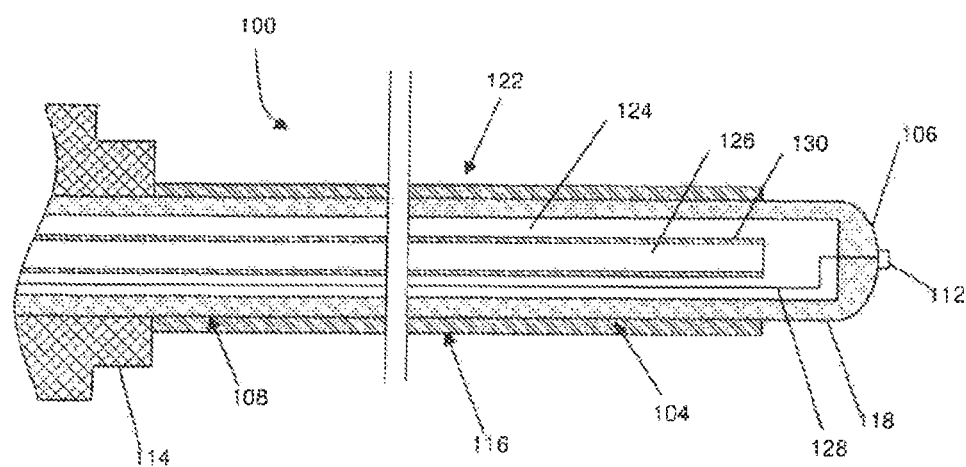
FIG. 1C is a cross-sectional view of the device of FIG. 1A taken along the line 1C-1C in FIG. 1B.

The internal structure of probe 100 is shown in FIG. 1C. The shaft of probe 100 defines a first lumen 124, and the proximal end 110 of probe 100 is open and in communication with lumen 124. The distal end 106 of probe 100 is closed. Probe 100 further comprises an internal cannula, cylinder, or tube 130 disposed within lumen 124, defining a second lumen 126. Internal tube 130 has an open distal end, which is located proximally to distal end 106 of probe 100, and an open proximal end. The proximal end of internal tube 130 is structured to be operatively connected to a source of cooling fluid. For example, hub 114 may be operable to connect internal tube 130 to a flexible tube. The proximal end of the flexible tube may be connected to the cooling source, for example a reservoir of fluid, whereby the flexible tube functions as an inflow tube for cooling fluid from the reservoir to probe 100. Thus, in use, fluid flows from the reservoir of fluid, through the flexible tube, and into internal tube 130. The fluid subsequently exits the distal end of internal tube 130, flows into lumen 124 of probe 100, and exits probe 100 via open proximal end 110. Open proximal end 110 is coupled to means for disposing of the fluid or for returning the fluid to the reservoir. For example, another flexible tube may operatively connect proximal end 110 to the reservoir, such that the flexible tube functions as an outflow tube for the cooling fluid.

Figure 2:
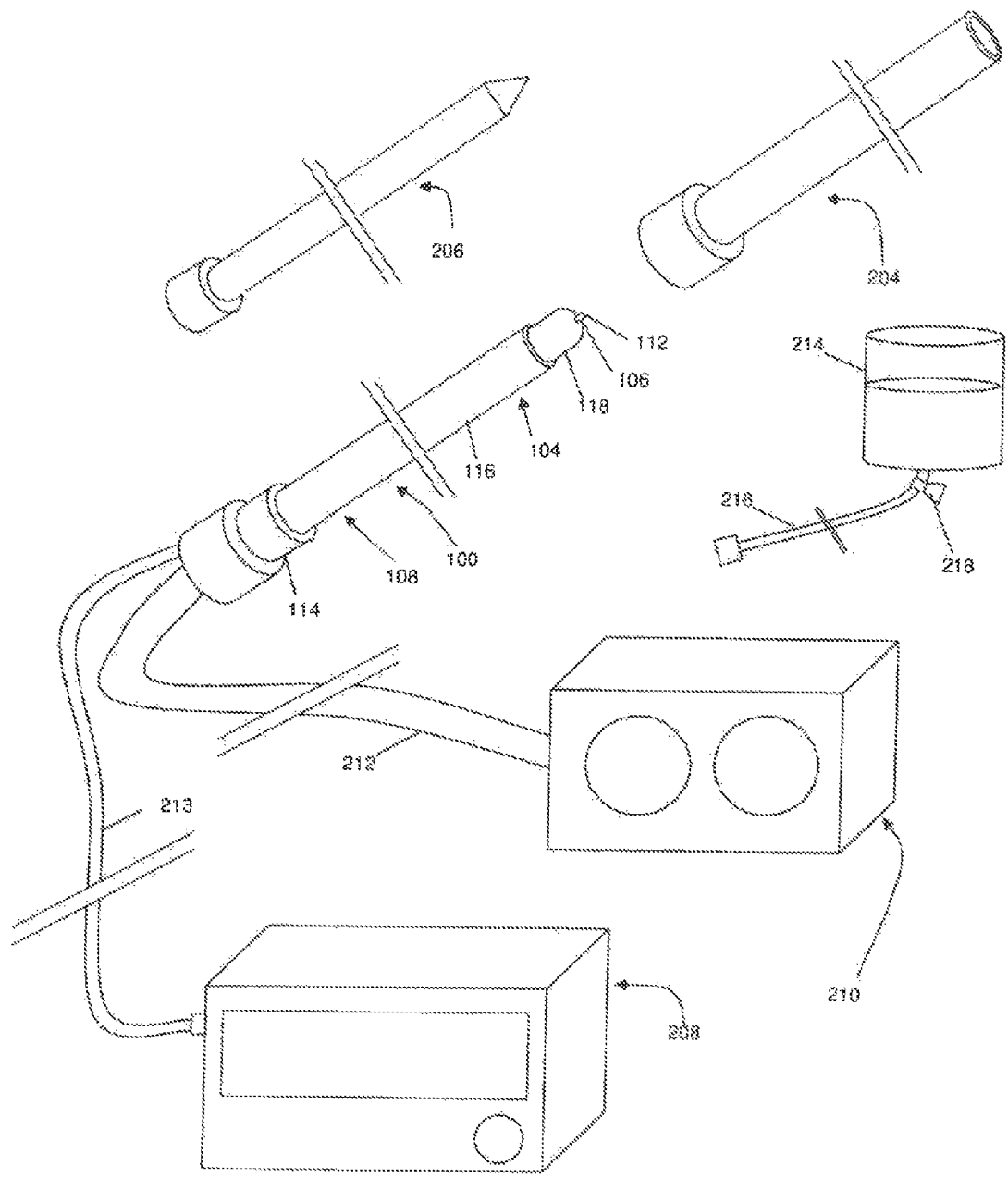
FIG. 2 is a perspective view of an embodiment of a system suitable for use with a method of the present invention.

As mentioned hereinabove, one or more fluids may be delivered from a reservoir to lumen 124 of probe 100 for the purposes of cooling probe 100. The fluid(s) may be delivered to the probe 100 via a number of means, and the invention is not limited in this regard. For example, in one embodiment and with reference to FIG. 2, the reservoir of fluid may comprise a container, for example an intravenous (IV) bag 214, which is elevated above the patient. Tubing 216, for example clear plastic flexible tubing, may be used to connect the reservoir to an inlet in probe 100. A valve 218 may be placed at the junction of the container and the tubing (or at some other location between the container and the probe), such that when the valve is opened, gravity may cause fluid to flow towards probe 100. After circulation within probe 100, fluid may exit probe 100 via tubing, which may drain into another reservoir, for example a second IV bag, or into a sink or other drain. In another embodiment, at least one pump may be used to deliver fluid to the probe 100. For example, at least one peristaltic pump 210 may be operatively connected to a reservoir of fluid. The reservoir of fluid may be an IV bag, a polypropylene vial or burette, or another container, for example. The pump(s) may pump the fluid from the reservoir to an inlet in probe 100. After circulating in probe 100, the fluid may exit the probe through an outlet in probe 100 and may flow through a tube to either the same or a different reservoir or, alternatively, to an alternate location as described above. A heat sink, heat exchanger, or other cooling source such as a refrigerant chiller may be used to cool the fluid after exiting the probe 100. A second pump, gravity, or a source of suction, for example, may assist in drawing the fluid out of the probe 100.

With reference again to FIGS. 1A-1C, probe 100 comprises a temperature sensing device 112. Temperature sensing device 112 may be any means for sensing and/or measuring temperature, including, but not limited to, a thermocouple, a thermistor, an optical fluorescence sensor, and a resistance thermometer. Temperature sensing device 112 is positioned at the distal region of probe 100, at distal end 106.

Probe 100 comprises means for operatively connecting temperature sensing device 112 to an external device. In some embodiments, such a device is a display or screen, such that the temperature measured by the temperature sensing device may be viewed by a user. In other embodiments, the external device is an electrical generator, such that temperature feedback may be provided to the electrical generator. Means for operatively connecting temperature sensing device 112 to an external device may comprise an insulated wire 128, which may extend proximally from temperature sensing device 112, through a lumen of probe 100 (such as the first lumen 124 as shown in FIG. 1C), and out of probe 100 through proximal end 110. Wire 128 may be any temperature or electrical conductor capable of operatively connecting temperature sensing device 112 to an external device. Alternatively, temperature sensing device 112 may be operatively connected to an external device via a wireless connecting means, including, for example, infrared or Bluetooth. Further details regarding temperature sensing devices may be found in U.S. patent application Ser. No. 11/105,490 (filed on Apr. 14, 2005), incorporated herein by reference.

With reference again to FIG. 2, an embodiment of a system suitable for use with probe 100 may comprise one or more of: one or more introducer apparatuses 204, for example a cannula 204; one or more dispersive return electrodes (not shown); one or more sources of cooling, for example pump 210; one or more energy sources, for example generator 208; and one or more connecting means, for example tube 212 and/or cable 213.

The introducer apparatus may aid in inserting probe 100 into a patient's body. The introducer apparatus may comprise a hollow elongate introducer or cannula 204 and an obturator 206. Further details regarding introducer apparatuses are disclosed in U.S. patent application Ser. No. 11/457,697 (filed on Jul. 14, 2006), previously incorporated herein by reference.

Probe 100 is structured to be operatively connected to an energy source, for example a generator 208. The connecting means for connecting probe 100 to generator 208 may comprise any component, device, or apparatus operable to make one or more electrical connections, for example an insulated wire or cable. In one embodiment, the connecting means comprises an electrical cable 213 terminating at hub 114 as well as a connector at a proximal end thereof. Cable 213 may be operable to couple to energy source 208 directly or indirectly, for example via an intermediate cable. At least one wire or other electrical conductor associated with cable 213 may be coupled to a conductive portion of shaft 122, for example by a crimp or solder connection, in order to supply energy from energy source 208 to shaft 122. In one specific embodiment, a 4-pin medical connector is used to connect cable 213 to an intermediate cable (not shown), which may be further attached to a 14-pin connector capable of being automatically identified when connected to generator 208. Further details regarding such an embodiment are disclosed in U.S. patent application Ser. No. 10/122,413 (filed on Apr. 16, 2002), incorporated herein by reference.

Generator 208 may produce various types of energy, for example microwave or radio-frequency electrical energy. In some embodiments, generator 208 produces radiofrequency electrical current, having a frequency of between about 10 kHz and about 1000 kHz, at a power of between about 1 W and about 50 W. An example of an RF generator that may be used as part of a system of the present invention is the Pain Management Generator (PMG) of Baylis Medical Company Inc. (Montreal, QC, Canada). Further details regarding embodiments of energy sources are disclosed in U.S. patent application Ser. No. 11/457,697 (filed on Jul. 14, 2006), previously incorporated herein by reference.

As mentioned hereinabove, in some embodiments, one or more peristaltic pumps 210 are used to supply a cooling fluid to and return a cooling fluid from probe(s) 100. In other embodiments, other types of pumps may be used. Examples include, but are not limited to, a centrifugal pump or a piston pump. As mentioned above with respect to temperature control, controlling the delivery of a cooling fluid, or other cooling means, may be performed for each probe independently, or the cooling may be controlled based on an average temperature measurement or a measurement recorded from one probe, for example. Further details regarding the cooling source are provided in U.S. patent application Ser. No. 11/105,527 (filed on Apr. 14, 2005) and Ser. No. 10/864,410 (filed on Dec. 10, 2005).

Methods

Embodiments of a method of the present invention allow for the creation of a lesion between an energy delivery portion of an electrosurgical device and some predetermined location, such as a segment of a thoracic vertebra. For example, a lesion may be created substantially distal to and facing the energy delivery portion by delivering energy to the energy delivery portion and cooling the energy delivery portion. This provides an advantageous benefit not found in the prior art, in that it obviates the need for a probe 100 to be placed in very close proximity to a target nerve in order to effectively lesion the target nerve.

In one broad aspect, an embodiment of a method of the present invention comprises positioning an energy delivery portion of an electrosurgical device to face a segment of a thoracic vertebra at a distance from the segment; and cooling the energy delivery portion and delivering energy through the energy delivery portion whereby a lesion is formed at least substantially distal to the energy delivery portion. In some embodiments the lesion is formed at a location at least between the energy delivery portion and the segment of the thoracic vertebra.

In one broad aspect, the present invention comprises a method for treating a thoracic region of a spine of a patient's body, for example in order to treat pain. Some embodiments of the method comprise inserting an electrosurgical device into a patient's body and positioning an energy delivery portion of the electrosurgical device in proximity to a medial branch of a thoracic dorsal ramus nerve such that the energy delivery portion is positioned at a distance from and facing a segment of a thoracic vertebra; delivering energy through and/while cooling the energy delivery portion to create a lesion at the medial branch of the thoracic dorsal ramus nerve. Preferably the lesion forms at least substantially distal to the energy delivery portion. In one example of the embodiment, the lesion forms between the energy delivery portion and a segment of the thoracic vertebra. As a feature of this aspect, the electrosurgical device may be inserted and positioned in a relatively safe, effective, and efficient manner.

In another broad aspect the embodiments of the present invention are directed to a method of treatment of the thoracic region of a patient's body where the method comprises inserting an introducer apparatus into the patient's body. The apparatus comprises a cannula and an obturator disposed within a lumen of the cannula the obturator protruding from a distal end of the cannula. The apparatus is positioned such that a distal tip of the obturator abuts a segment of the thoracic vertebra. An electrosurgical device is then inserted within the cannula to position an energy delivery portion of the device at a distance from the segment of the thoracic vertebra. The method further comprises delivering energy through the energy delivery portion and cooling the energy delivery portion whereby a lesion forms at least between the energy delivery portion and the segment of the thoracic vertebra.

In one embodiment of the present invention a marker is used in order to position the electrosurgical device. In some embodiments the marker may be used in order to position an introducer apparatus. Some embodiments of the method comprise positioning a marker such that a distal end of the marker abuts a segment of a thoracic vertebra, the marker functioning as a visual reference for positioning an electrosurgical device. When viewed under imaging, an electrosurgical device such as probe is advanced towards the marker to position the distal tip of the device at the distal end of the marker.

In some embodiments the target site is a superolateral aspect of a transverse process of a thoracic vertebra. In some such embodiments, the electrosurgical device is inserted into the patient's body such that at least a portion of the electrosurgical device is generally upstanding relative to a portion of the superolateral aspect. In some such embodiments, inserting the electrosurgical device comprises aligning the electrosurgical device such that it is oriented substantially away from an anterior-posterior axis of the patient's body, in a substantially cranial direction and advancing the electrosurgical device into the patient's body towards the superior aspect of the transverse process. The electrosurgical device is positioned such that the energy delivery portion of the device is at a distance from the superior-lateral portion of the transverse process. In one embodiment the energy delivery portion is cooled substantially while delivering energy, such a lesion forms at least substantially distal to the energy delivery portion.

In alternate embodiments, the electrosurgical device is inserted into the patient's body such that at least a portion of the electrosurgical device is positioned at a centroid of the transverse process. In some such embodiments, inserting the electrosurgical device comprises aligning an electrosurgical device substantially with an anterior-posterior axis of a patient's body; advancing the electrosurgical device into the patient's body towards the centroid of the transverse process; and positioning the energy delivery portion is in proximity to the superolateral aspect of the transverse process. The device is positioned such that an energy delivery portion of the device is positioned at a distance from the superolateral aspect of the transverse process. In one embodiment, the energy delivery portion of the device is cooled substantially while delivering energy, such that a lesion extends between the energy delivery portion and the superolateral aspect. In one example the lesion is formed at least substantially distal to the energy delivery portion.

In further embodiments, the target site is a lamina of the thoracic vertebra. In some such embodiments, the electrosurgical device is inserted into the patient's body such that at least a portion of the electrosurgical device is generally upstanding relative to a portion of the lamina. In some such embodiments, inserting the electrosurgical device comprises aligning the electrosurgical device such that it is oriented substantially away from an anterior-posterior axis of the patient's body, in a substantially lateral direction and advancing the electrosurgical device into the patient's body towards the lamina. In addition to embodiments described above, further embodiments of the present invention will be described herein below.

In one specific embodiment of the present invention, a method of lesioning a medial branch of a dorsal ramus nerve in a thoracic region of a patient's body is provided, the method comprising: visualizing a thoracic vertebra of the patient's body along an anterior-posterior axis of the patient's body using fluoroscopic imaging; positioning a spinal needle at a superolateral aspect of a transverse process of the thoracic vertebra under guidance of the fluoroscopic imaging; visualizing the thoracic vertebra along an axis about 45 degrees caudal to the anterior-posterior axis; inserting an introducer apparatus into the patient's body along the axis about 45 degrees caudal to the anterior-posterior axis, the introducer apparatus comprising an obturator disposed within a lumen of a cannula, the obturator protruding from a distal end of the cannula by about 7.5 mm; guiding the introducer apparatus towards a tip of the spinal needle; positioning a distal tip of the obturator in abutting relation to the superolateral aspect of the transverse process, in proximity to the tip of the spinal needle; removing the obturator from the lumen of the cannula; inserting an electrosurgical device through the lumen of the cannula, the electrosurgical device having an energy delivery portion at a distal tip of the electrosurgical device, the electrosurgical device protruding from the distal end of the cannula by about 5.5 mm, whereby the energy delivery portion of the electrosurgical device is facing the superolateral aspect of the transverse process and is located about 2 mm away from the superolateral aspect of the transverse process; and delivering radiofrequency electrical energy to the energy delivery portion of the electrosurgical device while cooling the energy delivery portion of the electrosurgical device.

Figure 3A:
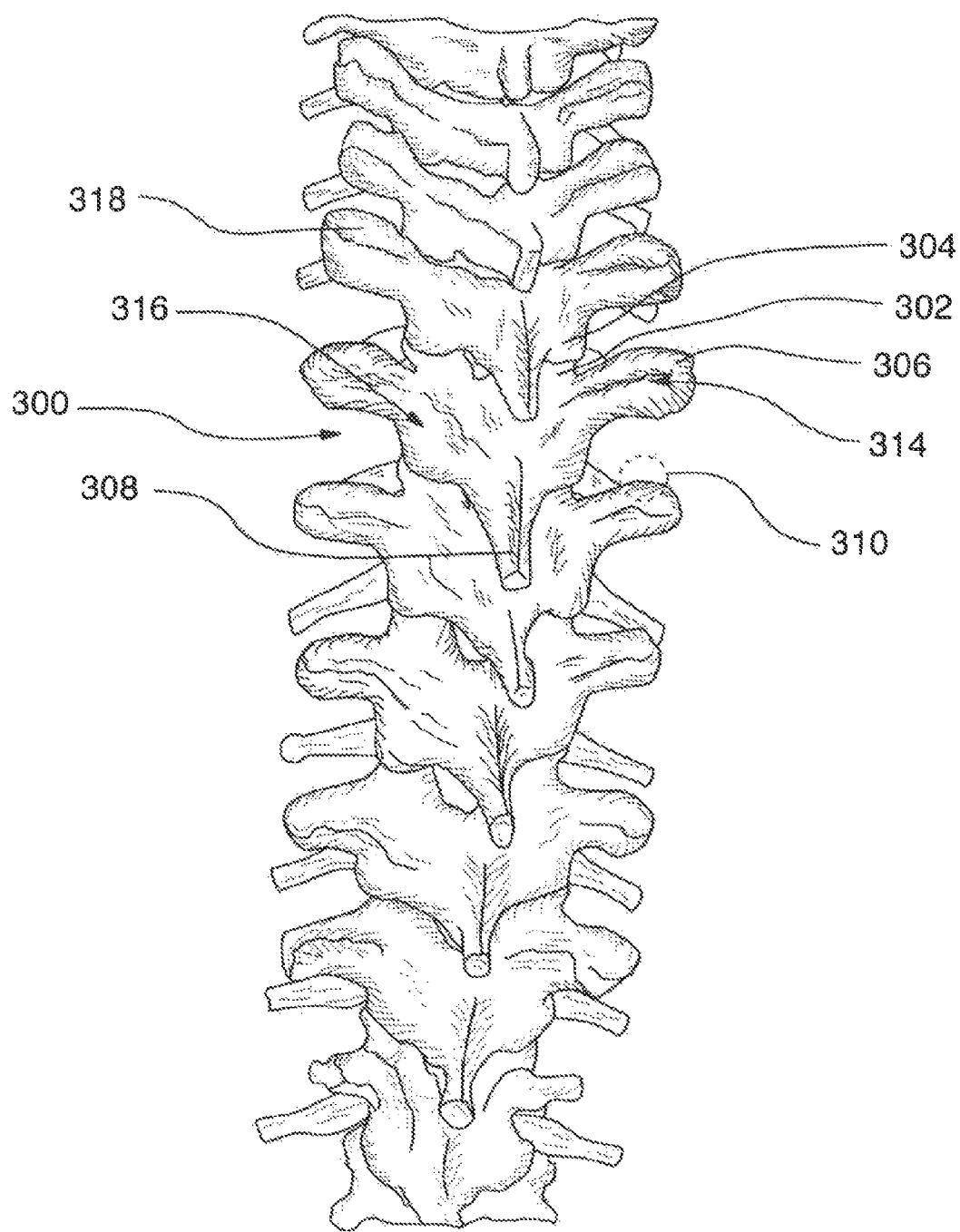
FIG. 3A is a view of the thoracic vertebrae of a patient's spine, showing a target site for energy delivery.

Referring now to FIG. 3A, a brief description of the typical anatomy of the thoracic region of the spine is provided. The vertebrae 300 of the thoracic region of the spine are intermediate in size between those of the cervical and lumbar regions; the upper thoracic vertebrae being smaller than those in the lower part of the thoracic region. The vertebral bodies are generally as broad in the anterior-posterior as in the transverse direction. At the upper and lower ends of the thoracic region the vertebral bodies resemble respectively those of the cervical and lumbar vertebrae. As shown in FIG. 3A, the pedicles of the thoracic vertebrae 300 are directed backward and slightly upward. The spinous process 308 is long and extends posterior and caudal, and ends in a tuberculated extremity. The thoracic facet joints are paired joints located between the superior 302 and inferior 304 articular processes of adjacent vertebrae. The superior articular processes 302 are thin plates of bone projecting upward from the junctions of the pedicles and laminae 316; their articular facets are practically flat, and are directed posteriorly and slightly lateral and upward. The inferior articular processes 304 are fused to a considerable extent with the laminae 316, and project slightly beyond their lower borders; their facets are directed anteriorly and slightly medial and downward. The transverse processes 306 arise from the arch behind the superior articular processes 302 and pedicles; they are directed obliquely backward and lateral.

The thoracic facet joints are innervated by the medial branches of the dorsal rami. The medial branches pass between consecutive transverse processes 306 and head medially and inferiorly, passing through the centroid region 314 of the transverse process 306. The medial branches innervate the facet joint at the level of their respective spinal nerve and the two facet joints below. For example, the T1 medial branch innervates both the T1-T2 as well as the T2-T3 facet joints. At T1 to T4 and T9 and T10, the medial branches cross the superior-lateral aspect 318 of the transverse process 306. At T5 to T8, the medial branches follow a similar course, but may remain suspended within the intertransverse space. At T11 and T12, the medial branch has a course akin to the lumbar medial branches such that they course posteriorly along the medial aspect of the transverse process 306, at the root of the superior articular process 302.

The medial branches of the dorsal rami assume a reasonably constant course for the upper thoracic and lower levels. Mid-thoracic medial branches follow a much more variable course and do not have a consistent osseous relation.

Two types of articular branches arise from the medial branches. Ascending branches arise from the medial branch as it passes caudal to the facet joint. These branches are short and they ramify in the inferior aspect of the facet joint capsule. A slender descending articular branch arises from the medial branch as it crosses the superolateral corner 318 of the transverse process 306. It follows a sinuous course between the fascicles of multifidus to reach the superior aspect of the capsule of the facet joint below (Chua and Bogduk, 1995). Thus, thoracic facet joints, much like lumbar facet joints, receive bisegmental innervation from medial branches of dorsal ramus of the upper segment and one or more cephalad levels. For example, the T5 medial branch innervates the T5-6 and T6-7 facets.

Figure 3B:
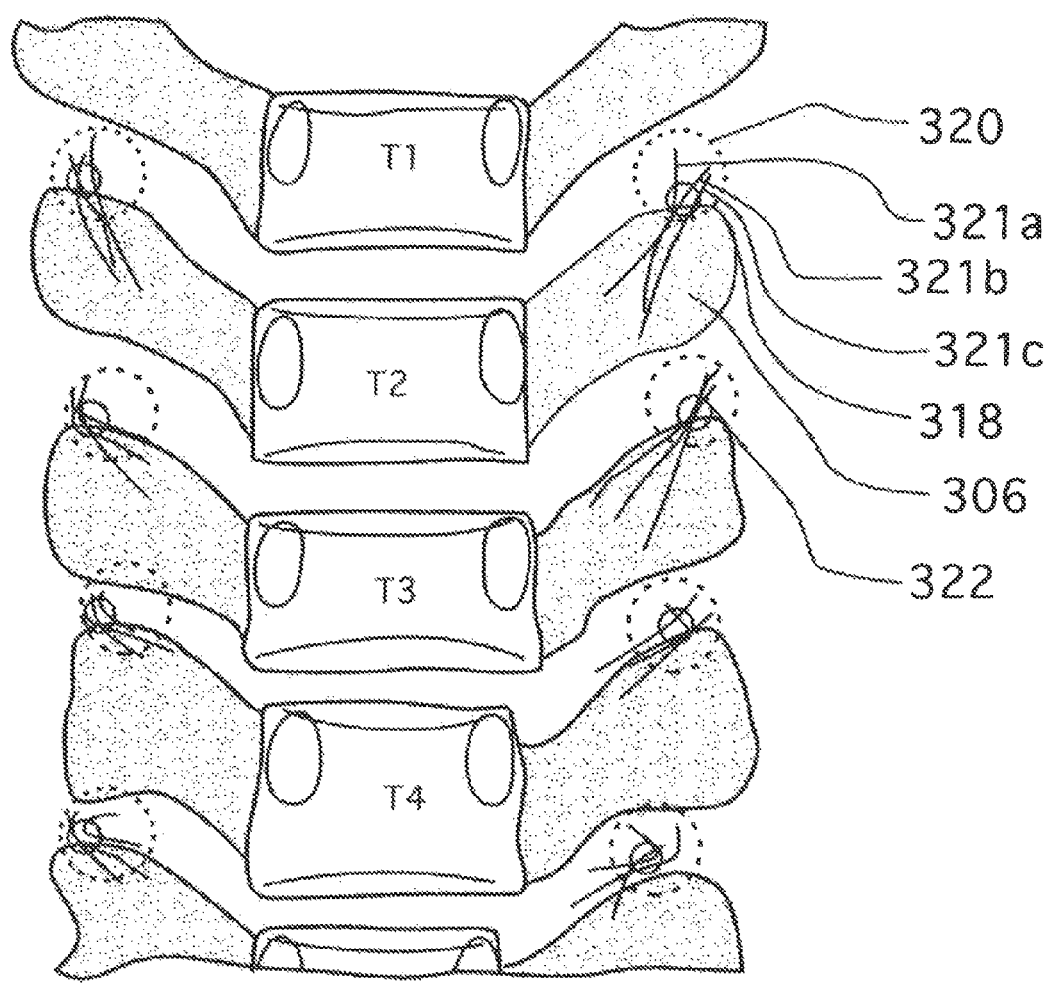
FIGS. 3B-3D are lateral views of the thoracic vertebrae showing the path of the nerves at the T1-T4, T5-T9 and T11-T12 thoracic levels.

Typically, in the T1-4 and T9-10 levels, the medial branch arises from the dorsal ramus within 5 mm of the lateral margin of the intervertebral foramen. The region 320 where the nerve is likely to be found is shown in FIGS. 3B and 3D. Upon leaving the intertransverse space, the medial branch 321 crosses the superolateral corner 318 of the transverse process 306 at its inflection point and then passes medially and inferiorly across the posterior surface of the transverse process 306 before ramifying into the multifidus muscles (not shown). Variability between individuals is minimal for the T1-T4 medial branches near the superolateral corner 318 of subjacent transverse process. Also, variability decreases greatly near the bone surface. The variability in the course of the medial branch is shown by the medial branches 321a, 321b and 321c of varying anatomies. Variability between individuals is minimal for the T9-T10 medial branches near the superolateral corner of subjacent transverse process as shown in FIG. 3D. The variability decreases greatly near the surface of the bone as shown by the path of the nerves in region 322. The reference numerals 321a, 321b and 321c indicate variable course of the nerve 321 in different individuals.

Figure 3C:
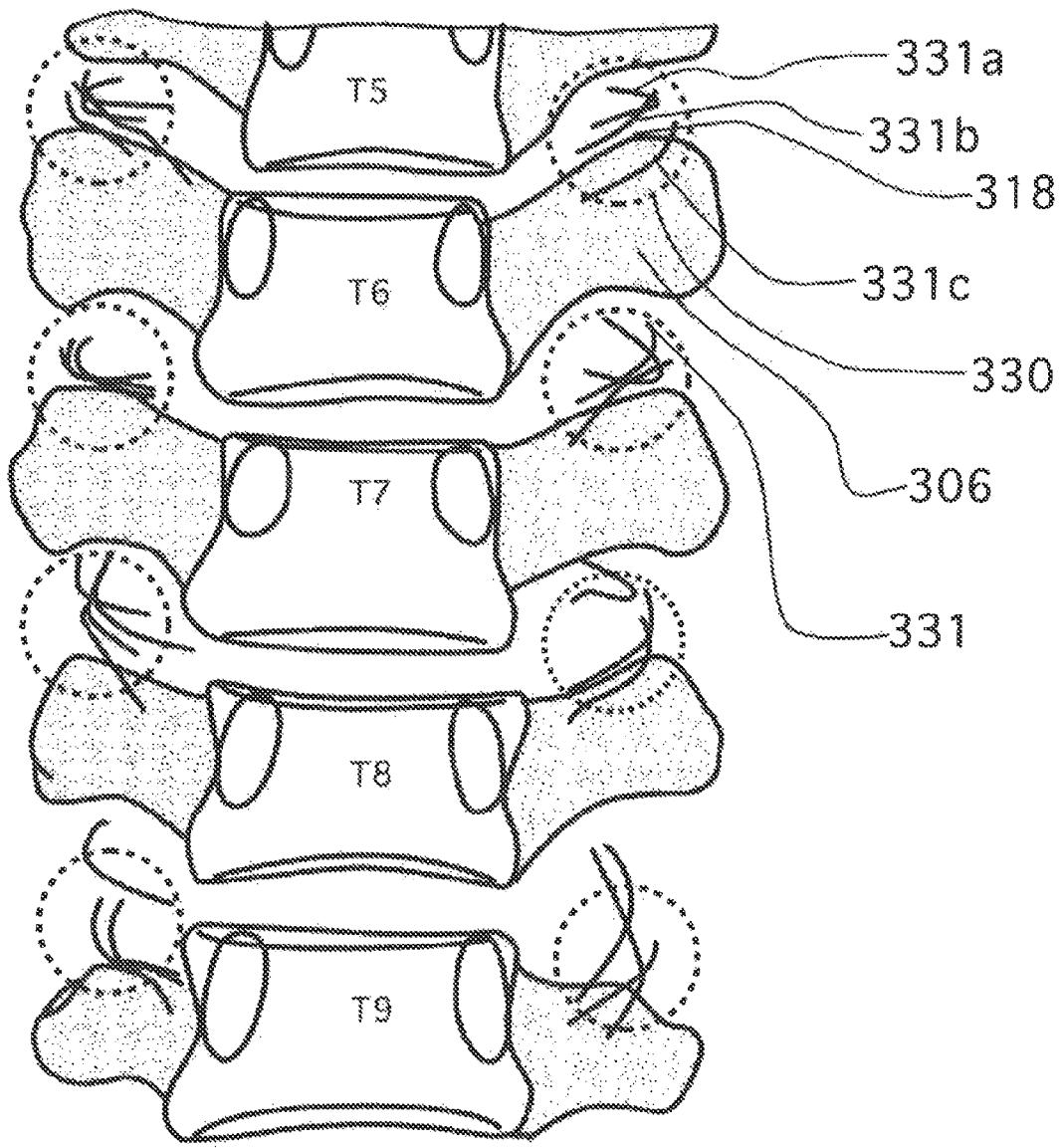
Figure 3D:
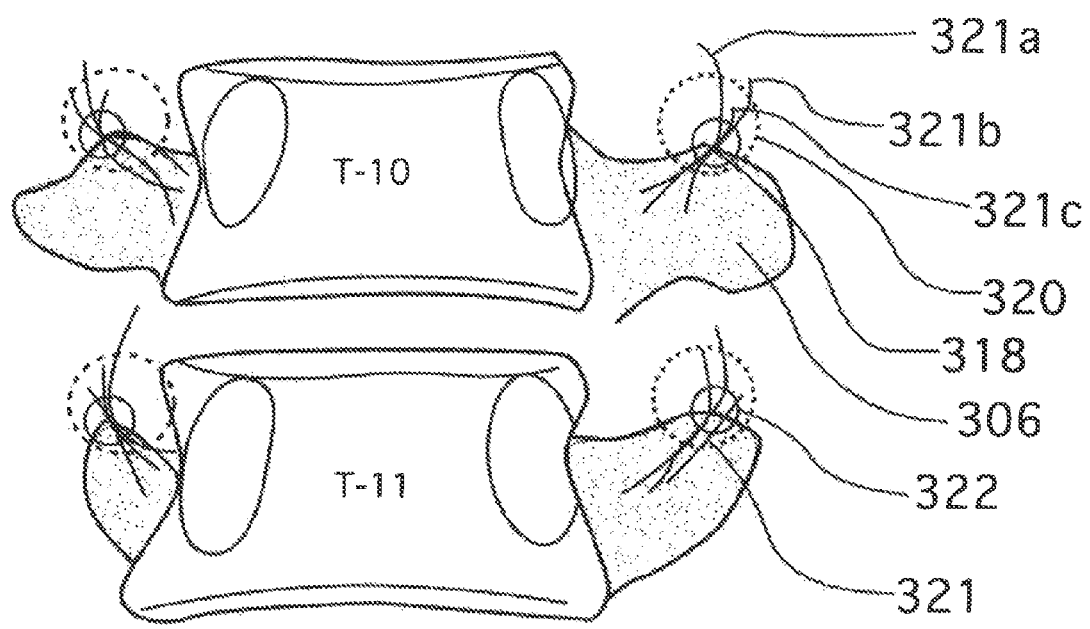

In the mid-thoracic levels from T5-8 as shown in FIG. 3C, exceptions to the archetypical course occur where, although the course is parallel, the nerve may be displaced superiorly and therefore may not contact the transverse process 306 (Chua and Bogduk, 1995). The likely course of the nerve is indicated by the region 330. Treatment at these levels is challenging as the nerve lacks a consistent osseus relation, which makes landmarking difficult. Variability between individuals is significant for the T5-T8 medial branch 331 near the superolateral corner of subjacent transverse process. The location of the medial branch may vary as indicated by the medial branches 331a, 331b and 331c in varying anatomies. Reference numerals 321a, 321b and 321c indicate variable course of the nerve 321 in different individuals.

At the T11 level, the medial branch runs across the lateral surface of the root of the superior articular process of the T12 (Chua and Bogduk, 1995). The T12 transverse process is much shorter than typical transverse processes. The T12 medial branch assumes a course analogous to the lumbar medial branches crossing the junction of the superior articular process and the transverse process (Chua and Bogduk, 1995).

Due to the varied course of the medial branch across the 12 thoracic levels, the lack of bony landmarks associated with the thoracic medial branch, and the anatomic differences among patients, it is often required to create several lesions in order to denervate one thoracic facet joint, as described by Dreyfuss et al (ISIS Newsletter, December 1997, Volume 2, Number 6). Embodiments of the present invention allow for the formation of a relatively large lesion for denervating a facet joint or for treating other pathologies associated with a medial branch, for example musculocutaneous or muscular pain, thus providing a more straightforward, safer, more effective and less invasive procedure.

Embodiments of a method of treating thoracic pain in accordance with the present invention will be presently described in greater detail. The description will reference the anatomy of the first through tenth thoracic vertebrae. In some embodiments, the target site for treating thoracic pain may comprise the nerves innervating the facet joint, i.e. the medial branches of the dorsal rami. As described hereinabove, these nerves may be located substantially laterally, between two consecutive transverse processes, or substantially adjacent the superior edge of a transverse process. Thus, in a first embodiment, the target site 310 for energy delivery may be the superolateral aspect 318 of the transverse process of a thoracic vertebra and the region immediately superior thereto.

The path of the nerves in the thoracic spine varies between the different thoracic levels. The path can also vary considerably between different individuals. Thus, in order to create an effective lesion, the electrosurgical device needs to be positioned to match the varying anatomies.

Embodiments of the present invention allow for effective treatment in the different thoracic levels. The use of cooling with standard RF allows the lesion to be formed substantially distal to the tip of the electrosurgical device. In some embodiments the lesion forms between the electrosurgical device and the thoracic vertebra. Furthermore, it allows for effective treatment of the target nerve when the electrosurgical device is positioned at a distance from the nerve. This ensures that the resulting lesion encompasses the target nerve, when the probe is positioned near the course of the target nerve. Thus embodiments of the present invention are directed to a system and method for providing an effective treatment of a target nerve in the thoracic region of the spine. More specifically, the method is directed to positioning an energy delivery portion of a device at a distance from a segment of a thoracic vertebra. and cooling the energy delivery portion such that a lesion forms substantially distal to the energy delivery portion.

As described in U.S. patent application Ser. No. 11/457, 697, previously incorporated herein by reference, in some embodiments, the step of inserting the electrosurgical device may comprise the use of an introducer apparatus to position the electrosurgical device at a distance from a segment of the thoracic vertebra. The apparatus may comprise a cannula and an obturator, for example. In use, the obturator may be initially disposed within a lumen of the cannula to facilitate insertion of the introducer apparatus to the target treatment site. Once the introducer apparatus has been properly positioned, the obturator may be removed and replaced within the cannula lumen by the electrosurgical device. Thus, rather than inserting and positioning the electrosurgical device as described hereinabove, the user may insert and position an introducer apparatus as described hereinabove. The user may then remove the obturator from the cannula, and insert the electrosurgical device through the cannula. For example, in the embodiment shown in FIG. 4, the user may insert an introducer apparatus such that it is generally upstanding relative to the superolateral aspect 318 of the transverse process 306, and advance the introducer apparatus until the distal end of the obturator contacts the superolateral aspect 318 of the transverse process 306. The user may then withdraw the obturator from the cannula, and insert electrosurgical device 400 into the cannula, such that energy delivery portion 402 is at or adjacent target site 310. In embodiments wherein an introducer apparatus is not used, electrosurgical device 400 may have a substantially sharp tip, and thus may be inserted and positioned as shown in FIGS. 4-7.

In some particular embodiments, wherein an introducer apparatus is used, the introducer apparatus and the electrosurgical device may be structured such that the obturator protrudes a greater distance from the distal end of the cannula than the electrosurgical device does, when fully inserted through the cannula, as described in U.S. patent application Ser. No. 11/733,515 (filed on Apr. 10, 2007), incorporated herein by reference. In such an embodiment, the introducer apparatus may be advanced until the distal end of the obturator contacts bone, for example the superolateral aspect 318 of the transverse process. The obturator may then be removed from the cannula, leaving the cannula in place, and the electrosurgical device may be inserted into the cannula. Due to the difference in length of the obturator and the electrosurgical device, when the electrosurgical device is fully inserted into the cannula, a gap will exist between the distal end of the electrosurgical device and the transverse process. The existence of this gap may ensure that when energy is delivered from the electrosurgical device, the lesion created does not extend too deeply into the bone thus limiting any unwanted necrosis of the bone. In addition, such an embodiment may allow for fluoroscopic visualization of an intended location of lesion formation, as is further detailed in U.S. patent application Ser. No. 11/733,515 (filed on Apr. 10, 2007), previously incorporated herein by reference. In one example of this embodiment the difference in the length of the electrosurgical device and the obturator is between about 0.5 mm to about 4 mm. Hence the energy delivery portion of the electrosurgical device is located at a distance of about 0.5 mm to about 4 mm away from the transverse process. In one particular example, the distance between the energy delivery portion and the transverse process is about 2 mm.

In some embodiments a marker may be used to assist in positioning an introducer apparatus. In some embodiments the marker may be used to position an electrosurgical device. The marker may be used in medical procedures requiring real-time imaging to aid in the positioning of medical devices at locations within a patient's body. More specifically, the marker may be used in regions of the body having few anatomical structures (such as bone) that are visible during imaging. In these body regions a landmark is not available to assist in positioning the device. Thus, while positioning an electrosurgical device, it may be difficult to ascertain if the device has penetrated a region of the body other than the target location. In some medical procedures, it is critical to avoid certain anatomical structures that are in close proximity to the target site. Thus, use of a marker to position the device may make the procedure safer and more effective. In some embodiments, the marker is a needle. More specifically, the needle, in some embodiments, is a finder needle. In other embodiments the needle may be a spinal needle. The needle can be inserted into the patient's body such that the distal end of the needle marks a target location. The needle may partially or fully comprise a radiopaque material. For example, in one embodiment the needle may comprise a radiopaque marker band at its distal end. The band may comprise of a radiopaque material such as platinum or tungsten. In other embodiments the needle may comprise stainless steel. When viewed under imaging, an electrosurgical device such as probe can then be advanced towards the needle such that an energy delivery portion of the device is positioned at or near the distal end of the needle, for example at a distance from a region of the thoracic vertebra. In one example, as described hereinabove, the energy delivery portion of the electrosurgical device is at its distal tip.

Figure 8B:
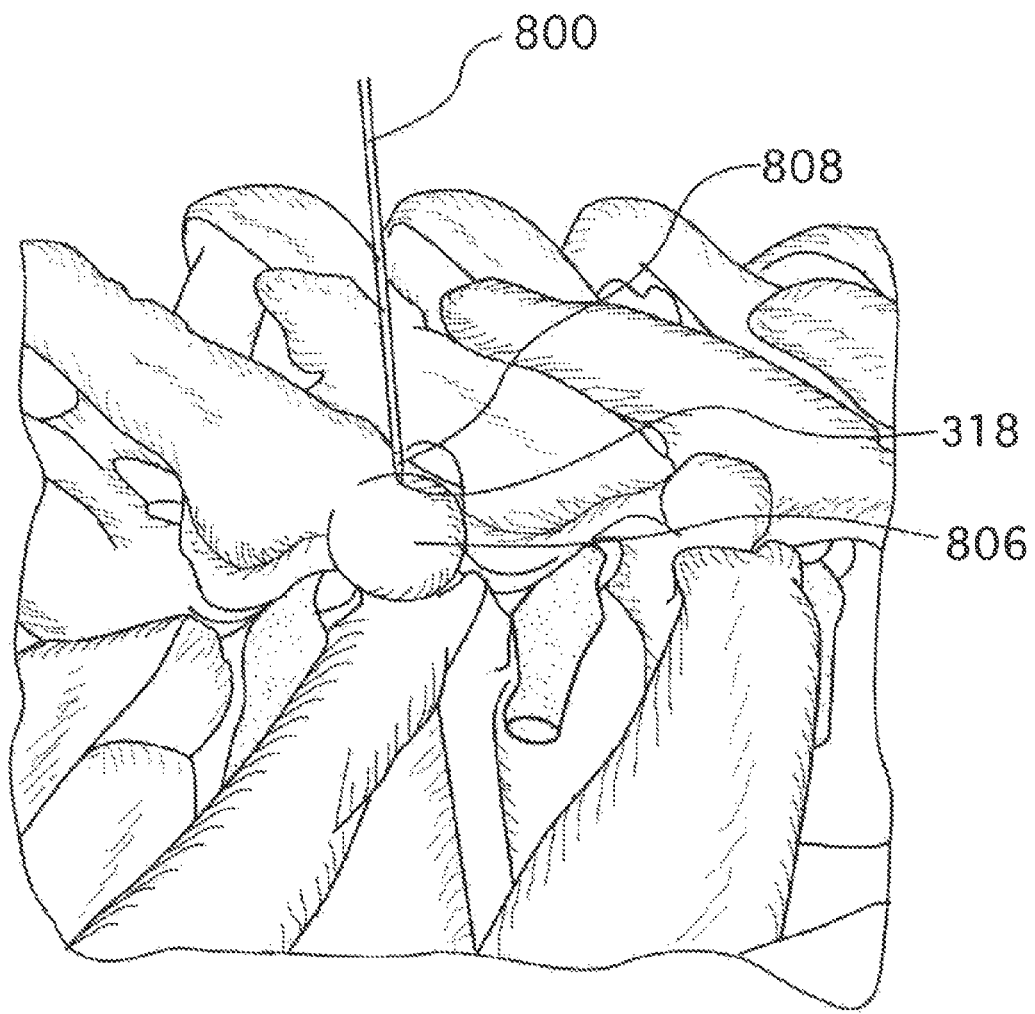
FIG. 8B is a lateral view of the thoracic vertebrae showing a spinal needle at the transverse process, in accordance with an embodiment of the present invention.
Figure 8A:
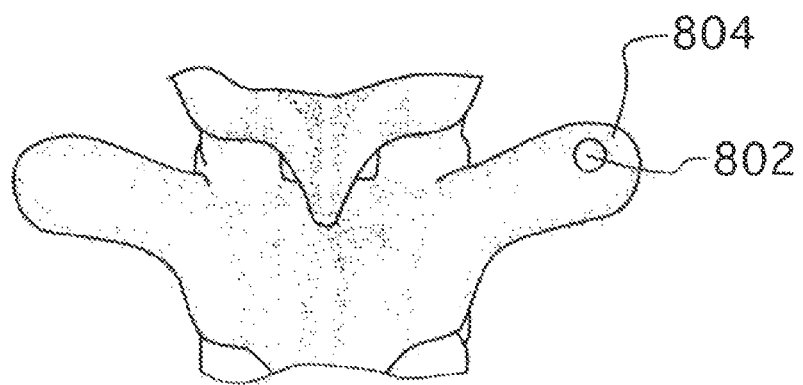
FIG. 8A illustrates the target location for inserting a spinal needle at the transverse process in accordance with one embodiment of the present invention.

Referring specifically now to FIGS. 8A-8B, in one embodiment, a spinal needle 800 may be used to guide the placement of the probe at the superolateral aspect 318 of the transverse process as illustrated in FIGS. 8A-8B. The distal end of the needle contacts a point 802 on the superior lateral outer third 804 on the posterior surface of the transverse process substantially towards the superior margin. More generally the needle is placed in the superior lateral quadrant of the transverse process. Before placement of the needle, the Anterior-Posterior image is aligned with the desired vertebral level using an imaging modality. In one example standard X-ray fluoroscopy is used. The needle which can be a thin spinal needle is placed on the patient's skin at a point above the superior lateral outer third 804 of the transverse process 806. The needle is then inserted into the patient's skin, and advanced until the tip 808 touches the transverse process 806. A lateral image is then obtained and placement of the needle ensures that the desired depth of the insertion of the probe is visible and is marked by the tip of the needle.

Once the needle has been positioned at the desired target location on the superior lateral quadrant of the transverse process, a medical instrument, for example, an introducer is used to find a suitable skin insertion point. The skin is nudged or depressed slightly using the instrument in order to visualize the insertion point using the lateral view. Using live fluoroscopy the angle of the introducer is adjusted until the tip 808 of the spinal needle is in the projected path of the introducer. The introducer is then removed and an introducer apparatus is inserted at the insertion site and its angle is adjusted such that the distal end of the introducer apparatus is targeted at the needle tip 808. The introducer apparatus is then advanced towards the tip of the spinal needle. The spinal needle helps prevent the device from being advanced further than the target site and reduces the risk of pleural puncture. In another example of the present embodiment the finder needle may be positioned on the lateral edge of the transverse process.

Figure 9A:
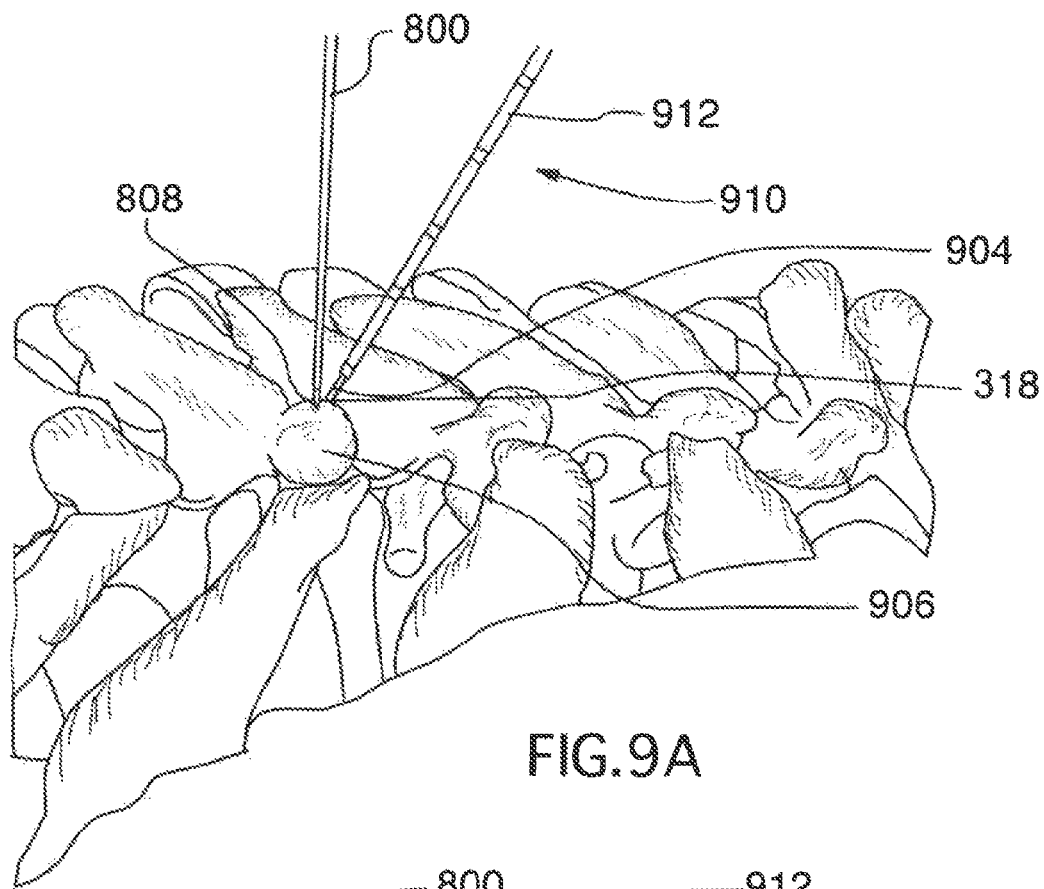
FIG. 9A is a lateral view of the thoracic vertebrae showing an introducer apparatus positioned at the tip of the spinal needle in accordance with an embodiment of the present invention.

The introducer apparatus is of the kind discussed previously in FIG. 4 and comprises an obturator 904 within the cannula 912. In one example of the present embodiment as illustrated in FIG. 9A, after the spinal needle has been positioned at the superior-lateral aspect of the transverse process, the C-arm is rotated 45° Cranially. Using a gun barrel approach, the introducer apparatus is advanced towards the tip 808 of the spinal needle under an Anterior-Posterior view. The apparatus is advanced until the obturator 904 touches the superior-lateral corner 918 of the transverse process 906 in proximity to the tip 808 of the spinal needle. After introducer placement, a lateral view is obtained to confirm appropriate positioning and depth.

Figure 9B:
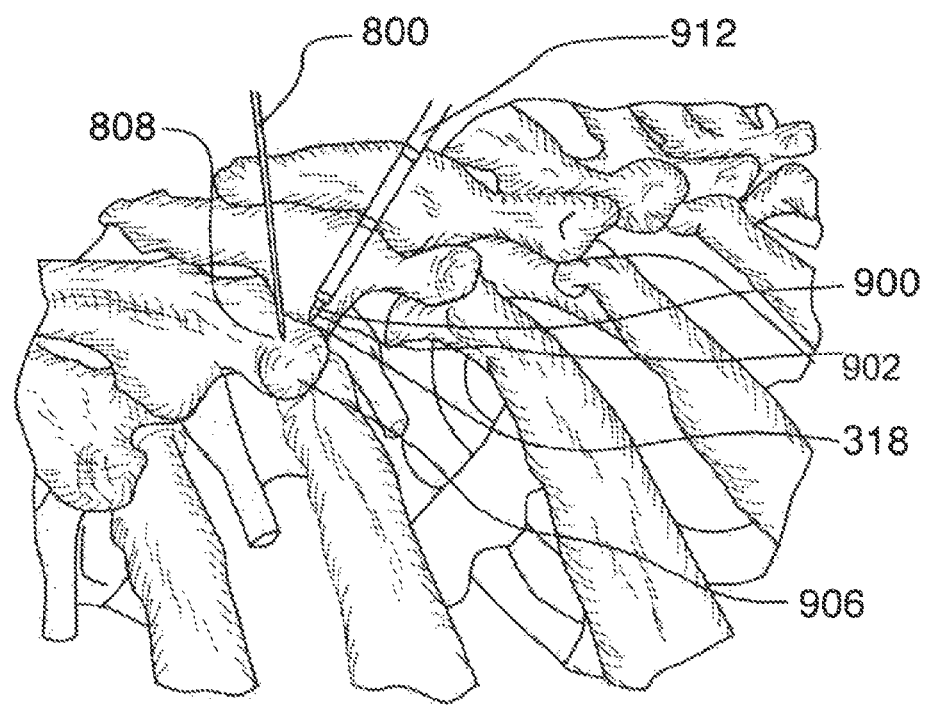
FIG. 9B is a lateral view of an electrosurgical device within a cannula, positioned at a distance from the transverse process in accordance with an embodiment of the present invention.
Figure 9C:
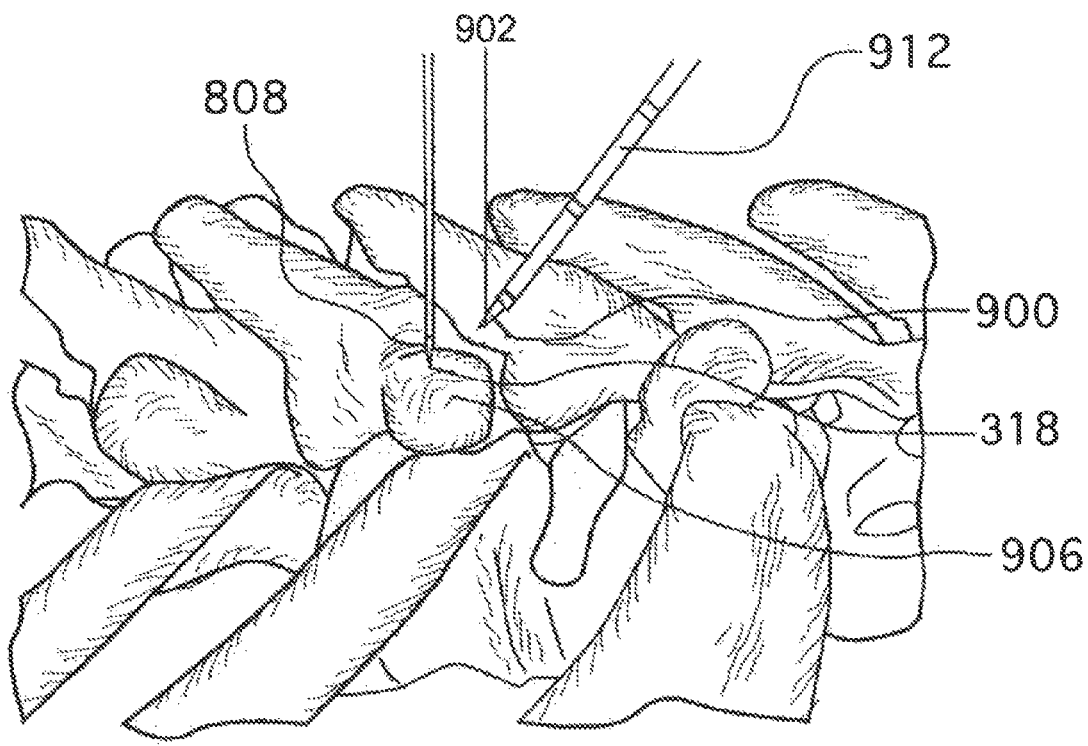
FIG. 9C is an oblique view of an electrosurgical device within a cannula, positioned at a distance from the transverse process in a accordance with an embodiment of the present invention.

The obturator is then removed and an electrosurgical device 900 is inserted into the cannula. The electrosurgical device protrudes a lesser distance from the distal end of the cannula than the obturator as shown in FIGS. 9B and 9C. As a result the distal tip 902 of the electrosurgical device is positioned a distance away from the superior-lateral aspect of the transverse process. Hence, the difference between the length of the obturator 904 and the electrosurgical device 900, automatically positions the device 900 such that the lesion forms at least partially in the intertransverse space. Energy is delivered from the distal tip of the device and the device is cooled, such that a lesion forms at least substantially distal to the distal tip 902 of the device. In one example the lesion is formed between the device distal tip 902 and the superior-lateral aspect. Additionally, use of the needle reduces the risk of pleural puncture as the device is not advanced past the distal end of the needle. In some embodiments an electrosurgical device may be inserted directly without the aid of an introducer apparatus. The electrosurgical apparatus may be positioned in a similar manner described above for the introducer apparatus with the aid of a spinal needle.

Various embodiments of the method of the present invention will be presently described, referring to various points/angles of insertion as well as various desired positions of the energy delivery portion of the electrosurgical device.

Figure 4:
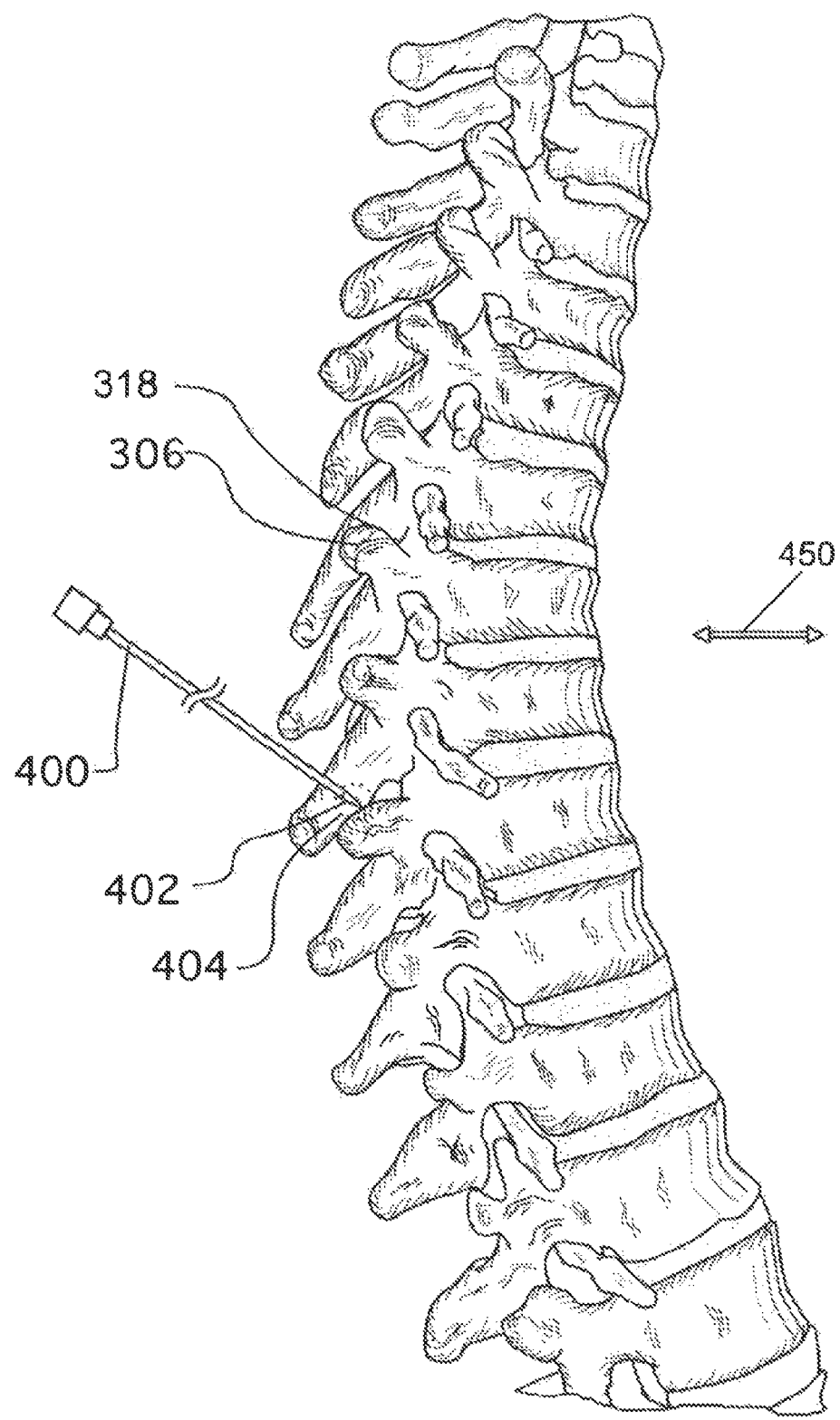
FIG. 4 illustrates a position of an electrosurgical device with respect to the thoracic vertebrae in accordance with an embodiment of a method of the present invention.

In some embodiments of the present invention an electrosurgical device may be inserted to the superior-lateral corner of the transverse process, as shown in FIG. 4. In some embodiments the electrosurgical device is inserted with the aid of an introducer apparatus as discussed previously herein. In some embodiments the patient may be placed in the prone position in preparation for the treatment procedure. The user may optionally administer various treatments, such as anesthetics or antibiotics, for example. In addition, as described above, the user may optionally insert a spinal needle into the patient's body, at the lateral edge of the transverse process, in order to act as a visual marker when the patient's body is visualized from angles other than the anterior-posterior view using a medical imaging system, for example a fluoroscopic system. The user may then insert at least one electrosurgical device 400, having an energy delivery portion 402, percutaneously toward the target site. In some embodiments, electrosurgical device 400 may be probe 100 described hereinabove. In other embodiments, electrosurgical device 400 may be, for example, an alternate device as described in U.S. patent application Ser. No. 11/457,697, previously incorporated herein by reference.

Prior to inserting electrosurgical device 400 into the patient's body, electrosurgical device 400 may be positioned at a point of insertion on a surface of the patient's body, for example on the dorsal surface. In one embodiment, the point of insertion on the patient's body may be the region that is substantially laterally aligned with a location medial to a lateral edge of the transverse process of the underlying thoracic vertebra.

When the electrosurgical device 400 has been positioned at the point of insertion, the electrosurgical device 400 may be inserted into the body. In one embodiment, electrosurgical device 400 may be inserted such that at least a portion of the electrosurgical device is generally upstanding relative to a superolateral aspect 318 of a transverse process 306 of a thoracic vertebra. As used herein, the term 'generally upstanding' refers to an angle that is between about 45.degree. and about 135.degree. from the horizontal plane. More specifically, in some embodiments, the term 'generally upstanding' may refer to an angle of between about 75.degree. and about 105.degree. from the horizontal plane. In some particular embodiments, the term 'generally upstanding' may refer to an angle of about 90.degree. from the horizontal plane. In some embodiments, wherein the electrosurgical device is bent or curved, as described in U.S. patent application Ser. No. 11/457,697 (filed on Jul. 14, 2006), previously incorporated herein by reference, the portion of the electrosurgical device that is distal to the bend or curve may be generally upstanding relative to the superolateral aspect 318 of the transverse process 306. In order to position electrosurgical device 400 such that it is generally upstanding relative to a superolateral aspect 318 of a transverse process 306 of a thoracic vertebra, electrosurgical device 400 may be angled such that it is oriented substantially away from an anterior-posterior (AP) axis 450 of the body, in a substantially cranial direction. In some embodiments, the electrosurgical device may be oriented at an angle of between about 15.degree. and about 60.degree. away from the AP axis in a substantially cranial direction. More specifically, electrosurgical device 400 may be oriented at an angle of about 45.degree. away from the AP axis, in a substantially cranial direction. Electrosurgical device 400 may be advanced until it contacts the superolateral aspect of the transverse process, such that energy delivery portion 402 is in proximity to the target site 310. The energy delivery portion is positioned at a distance from the superior-lateral aspect of the transverse process. In one embodiment an energy delivery portion of the electrosurgical device is positioned wherein is positioned at a location in the region bounded by a superior margin of the transverse process, an inferior margin of a superjacent transverse process, an anterior margin of the transverse process and an anterior margin of the superjacent transverse process, a posterior margin of a spinous process of the thoracic vertebra, an inferior articular process of the thoracic vertebra and a superior articular process of a superjacent thoracic vertebra, a lateral margin of the transverse process and a lateral margin of the superjacent transverse process.

When energy is applied to the energy delivery portion and it is substantially cooled, a lesion forms substantially distal to the energy delivery portion. The lesion is formed such that a significant portion of the lesion forms distal to the energy delivery portion.

Figure 5A:
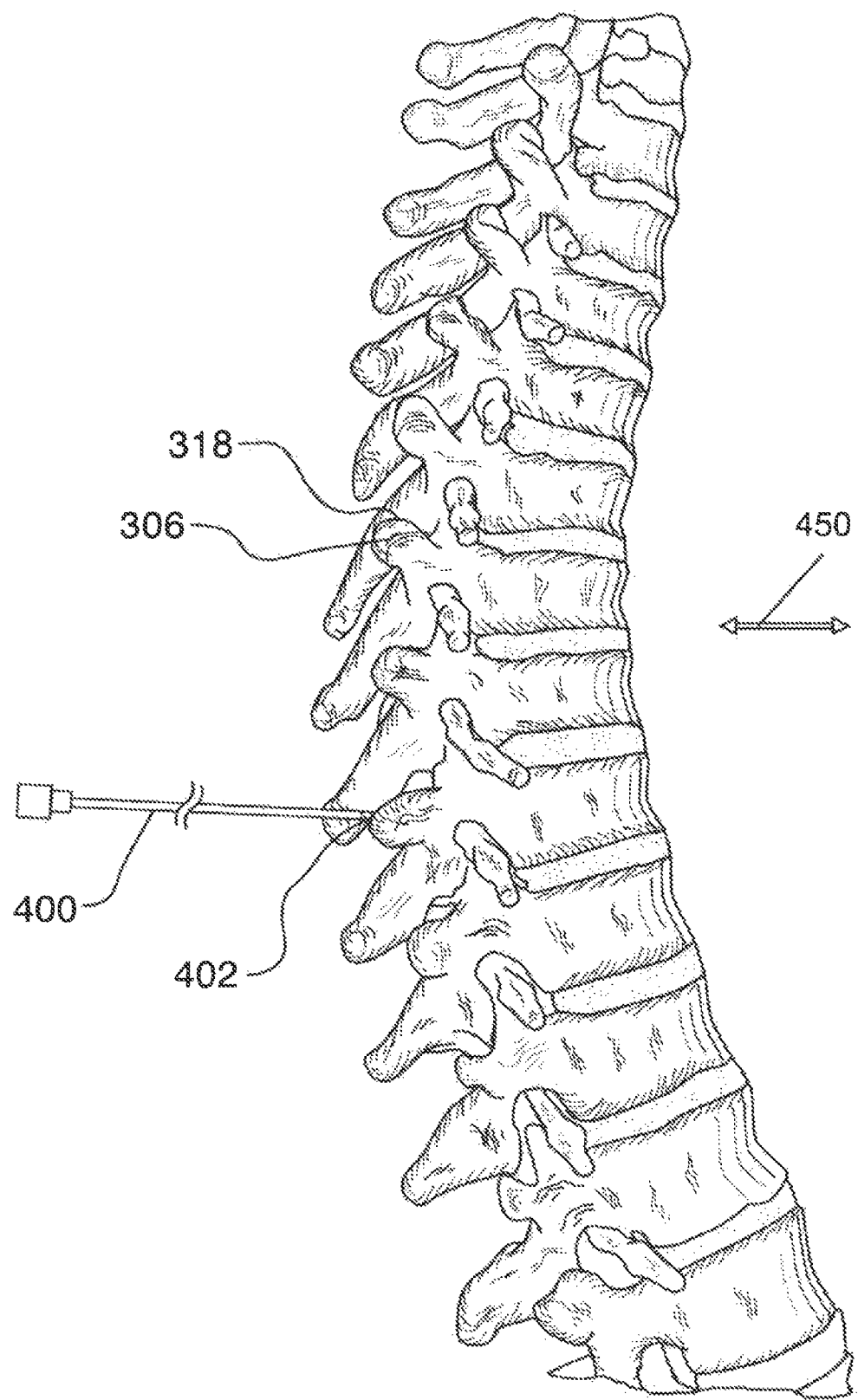
FIGS. 5A-5D illustrate steps involved in positioning an electrosurgical device in accordance with an embodiment of a method of the present invention.
Figure 5B:
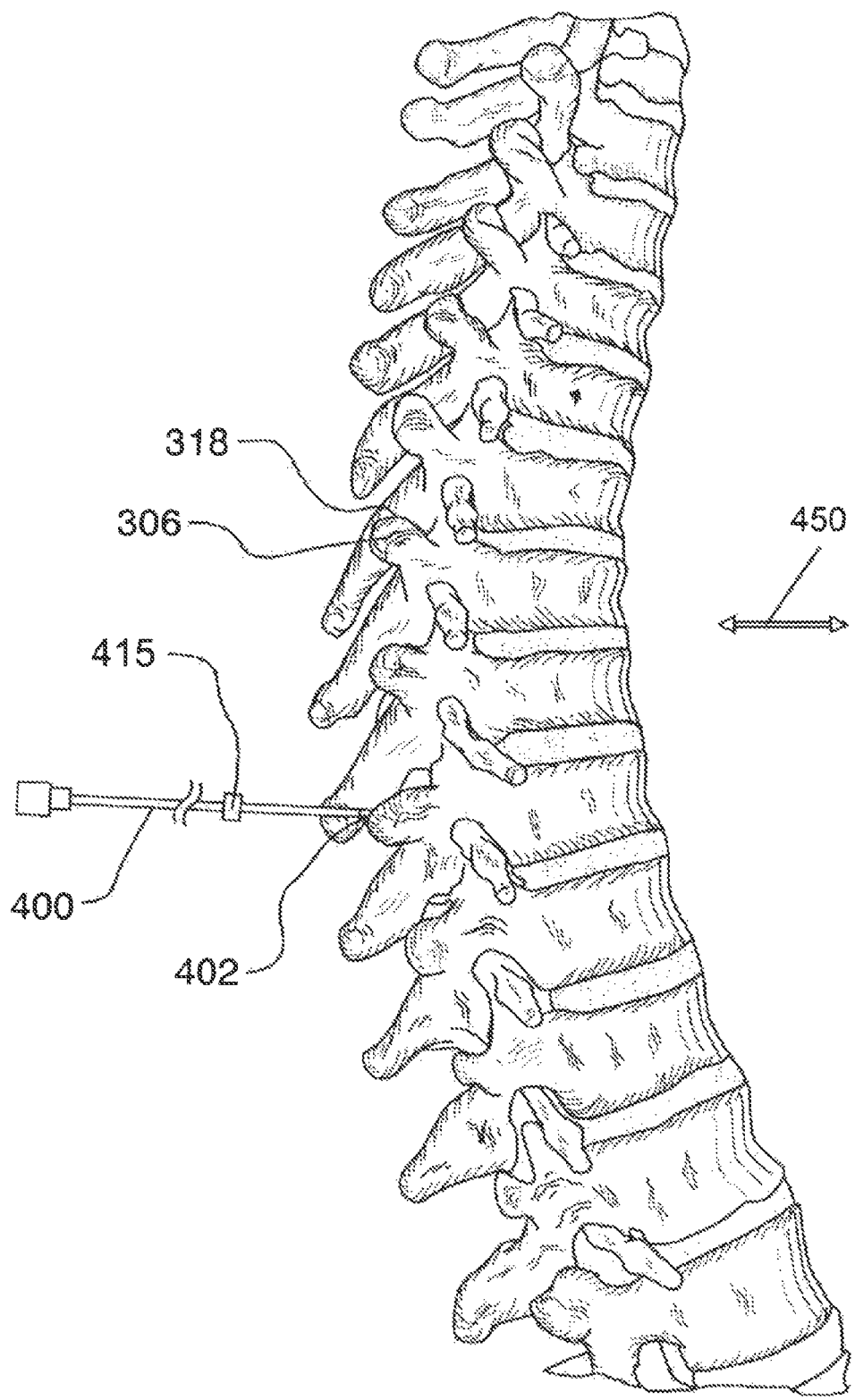
Figure 5C:
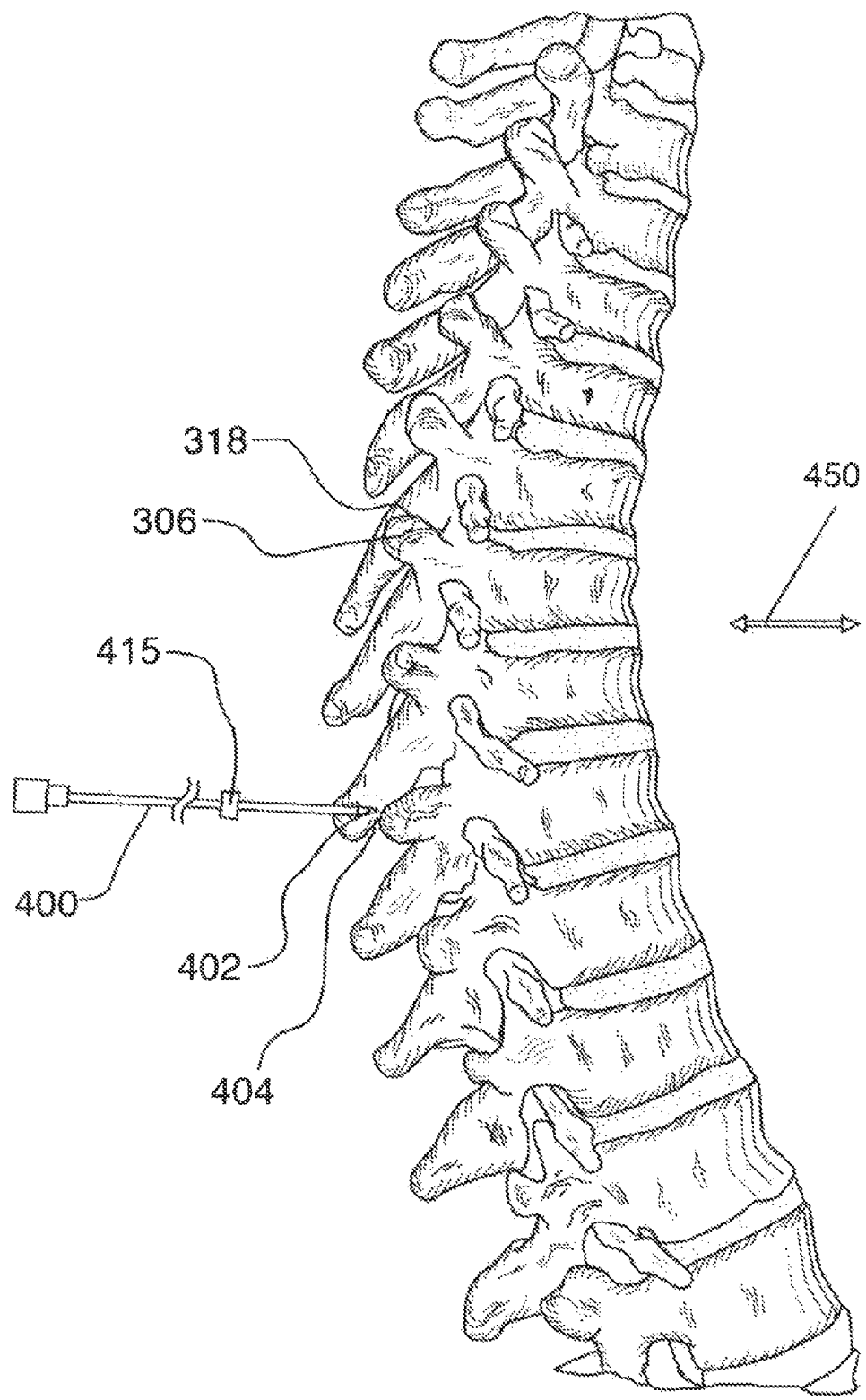

Referring to FIGS. 5A-5C, in an alternate embodiment, electrosurgical device 400 may be inserted into the patient's body such that it is substantially aligned with the AP axis 450 of the patient's body. In such an embodiment, electrosurgical device 400 may be inserted until the distal end contacts the centroid region 314 of the transverse process 306, as shown in FIG. 5A. In some embodiments and introducer apparatus may be used in order to position the electrosurgical device as discussed herein above. When electrosurgical device 400 contacts the centroid region 314 of the transverse process 306, a depth stopper 415, shown in FIG. 5B, may be placed on electrosurgical device 400 at the position on electrosurgical device 400 that is adjacent to the surface of the patient's skin (not shown). Electrosurgical device 400 may then be withdrawn slightly, for example by about 1 mm to about 5 mm. The user may then move electrosurgical device 400 in a substantially cranial direction until the distal end of electrosurgical device 400 is adjacent the superolateral aspect 318 of the transverse process 306. In other words, the user may "walk" the electrosurgical device in the cranial direction, until the distal end of the electrosurgical device slips over the superolateral aspect 318 of transverse process 306. The electrosurgical device may then be advanced slightly, until depth stopper 415 on electrosurgical device 400 is again adjacent the surface of the patient's skin, as shown in FIG. 5C, such that an energy delivery portion, for example the energy delivery portion 402 is in proximity to a target site. The electrosurgical device is positioned such that the energy delivery portion is positioned at a distance from the superolateral aspect. Energy is delivered from the energy delivery portion and the energy delivery portion is substantially cooled such that a lesion forms substantially distal to the energy delivery portion.

Figure 5D:
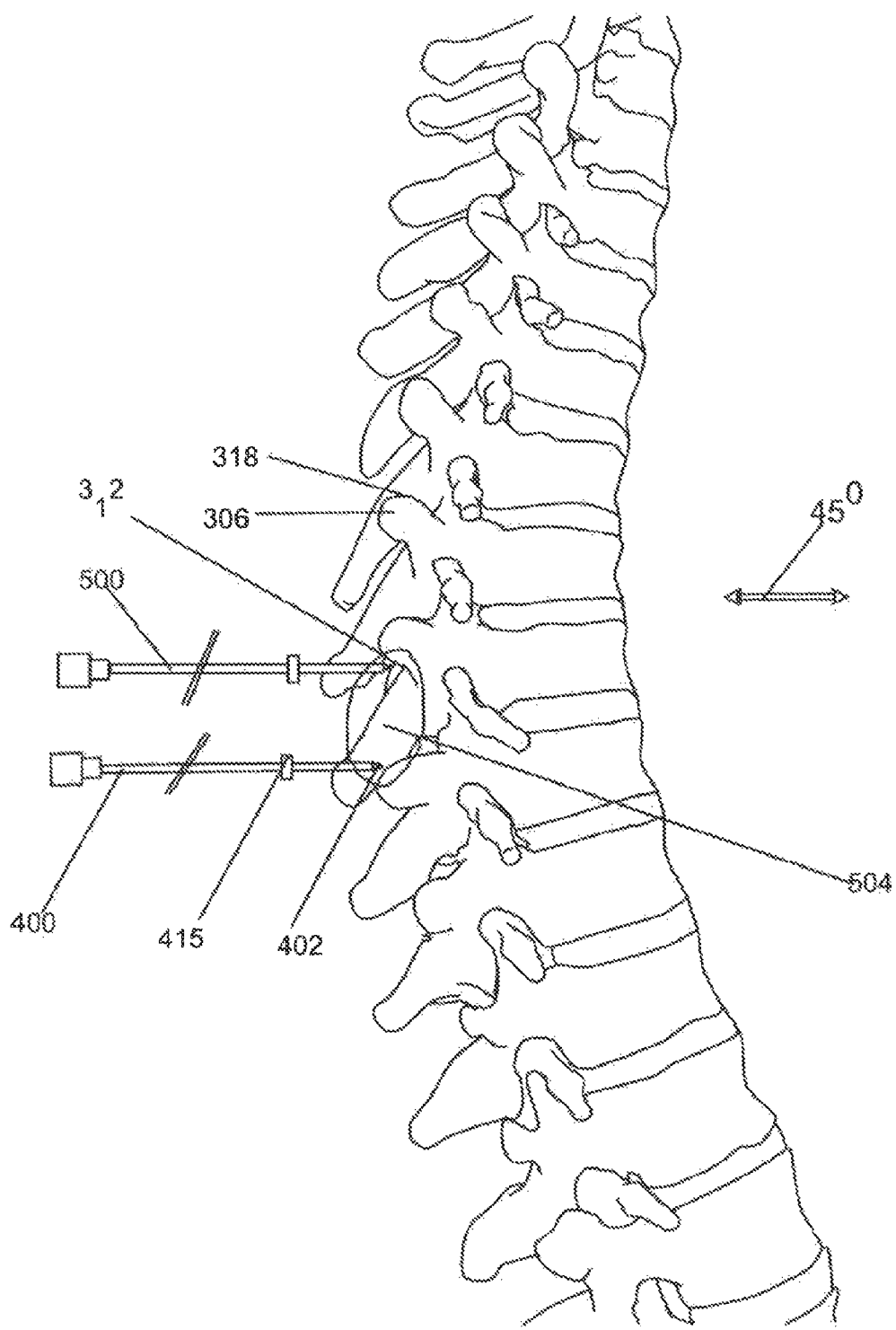

Alternatively, in some such embodiments, a user may insert a second electrosurgical device into the patient's body, at the vertebra that is immediately superior to the vertebra where the first electrosurgical device was inserted. For example, if the first electrosurgical device was inserted at T5, the second electrosurgical device may be inserted at T4. The second electrosurgical device may be inserted in the same manner as described with reference to FIGS. 5A-5C; however, rather than walking the second electrosurgical device in a cranial direction, the second electrosurgical device 500 may be walked in a caudal direction until the second electrosurgical device begins to slip over the inferolateral aspect 312 of the transverse process as shown in FIG. 5D. Thus, the first and second electrosurgical devices will be positioned at either end of an intertransverse space of adjacent vertebrae. In such an embodiment, energy may be delivered in a bipolar manner, such that a lesion 504 forms substantially between the first electrosurgical device and the second electrosurgical device. In some embodiments, the order of insertion is reversed, i.e. the first electrosurgical device is inserted to a thoracic vertebra and walked in a caudal direction and the second electrosurgical device is inserted to the immediately inferior vertebra and is walked in a cranial direction.

In a further alternate embodiment, electrosurgical device 400 may be inserted into the patient's body such that it is tilted substantially away from the AP axis 450 of the patient's body, in a substantially caudal direction. In some embodiments, the electrosurgical device may be oriented at an angle of between about 15.degree. and about 60.degree. away from the AP axis 450 in a substantially caudal direction. More specifically, electrosurgical device 400 may be oriented at an angle of about 45.degree. away from the AP axis, in a substantially caudal direction. In such an embodiment, electrosurgical device 400 may be inserted until the distal end contacts the centroid region 314 of the transverse process 306. When electrosurgical device 400 contacts the centroid region 314 of the transverse process 306, a depth stopper 415 may be placed on electrosurgical device 400 at the position on electrosurgical device 400 that is adjacent to the surface of the patient's skin (not shown). Electrosurgical device 400 may then be withdrawn slightly, for example by about 1 mm to about 5 mm. The user may "walk" the electrosurgical device in the cranial direction, until the distal end of the electrosurgical device begins to slip over the superolateral aspect 318 of transverse process 306. The electrosurgical device may then be advanced slightly, until depth stopper 415 on electrosurgical device 400 is again adjacent the surface of the patient's skin. Due to the caudal tilt of electrosurgical device 400, energy delivery portion 402 will extend substantially into the intertransverse space such that it is positioned at a distance from the superior-lateral aspect. After positioning the device, energy is delivered from the energy delivery portion and the energy delivery portion is cooled, such that a lesion forms at least substantially distal to the energy delivery portion.

The introducer apparatus discussed previously may be particularly useful in the embodiment described above wherein the electrosurgical device is oriented caudally away from the AP axis 450 of the patient's body, inserted towards the centroid of the transverse process, and walked cranially such that the energy delivery portion extends into the intertransverse space. Similar to the embodiments disclosed previously, the use of a longer obturator to position the cannula helps to minimize the depth into the intertransverse space to which the electrosurgical device extends, thus providing a safer procedure. In other words, the cannula and obturator are inserted until the obturator contacts the centroid, at which point a depth stopper may be positioned on the cannula at the patient's skin. The introducer apparatus (i.e. the cannula and obturator) is then walked cranially until the intertransverse space is reached. The obturator is then removed, leaving the cannula in place. When the electrosurgical device is thereafter inserted through the cannula, it will not extend substantially into the intertransverse space, since it is shorter than the obturator, thus resulting in a safer procedure. In some embodiments the electrosurgical device is about 0.5 to about 5 mm shorter than the obturator. Thus, the use of an obturator that is longer that the electrosurgical device, allows for the positioning of the electrosurgical device at a distance away from a segment of a thoracic vertebra in accordance with the embodiments of the present invention. In one example the difference in the length of the obturator and the electrosurgical device is about 2 mm, allowing for the positioning of the electrosurgical device at a distance of about 2 mm from the superior-lateral aspect.

Figure 6:
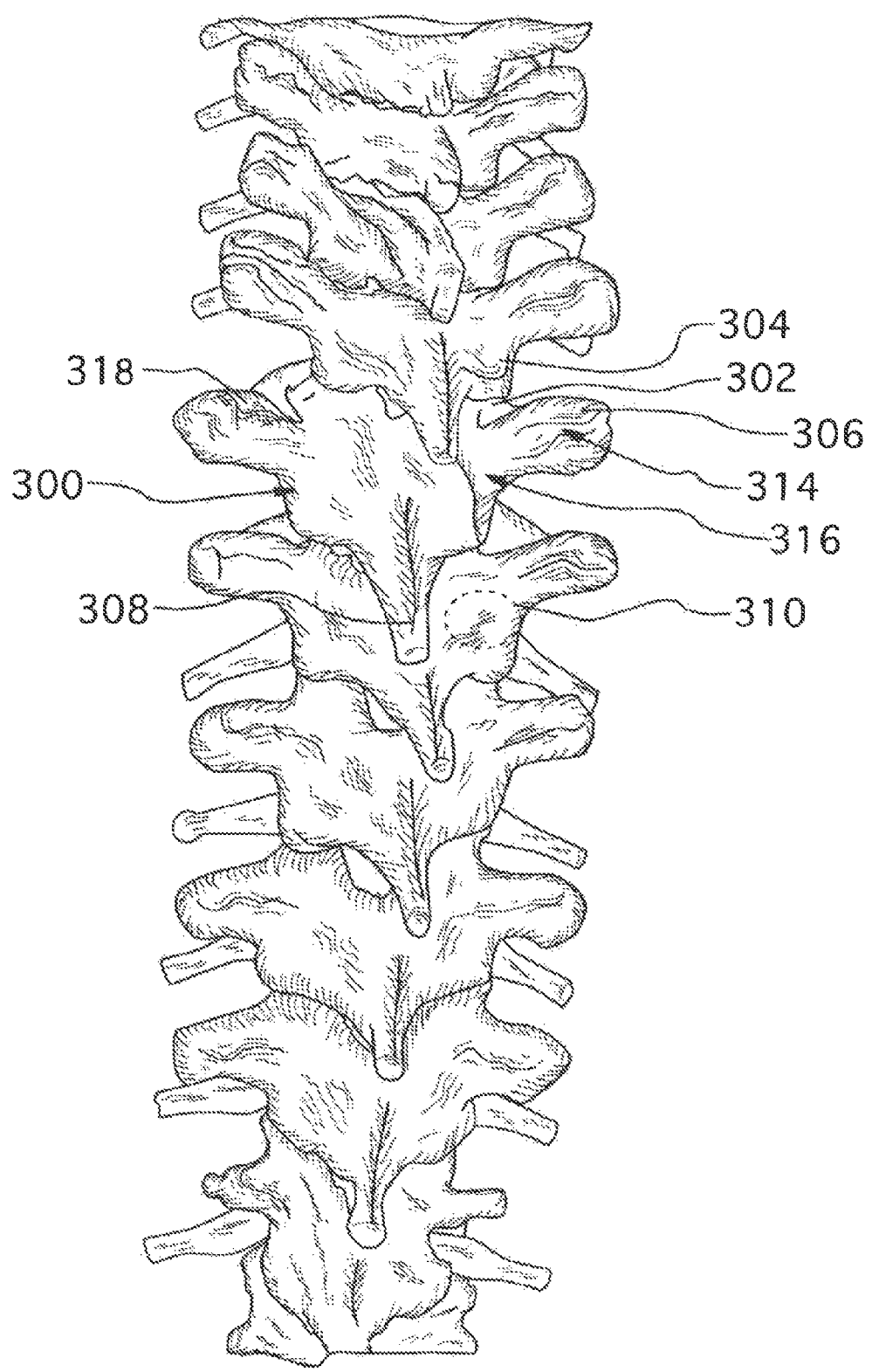
FIG. 6 is a view of the thoracic vertebrae of a patient's spine, showing an alternate target site for energy delivery.
Figure 7:
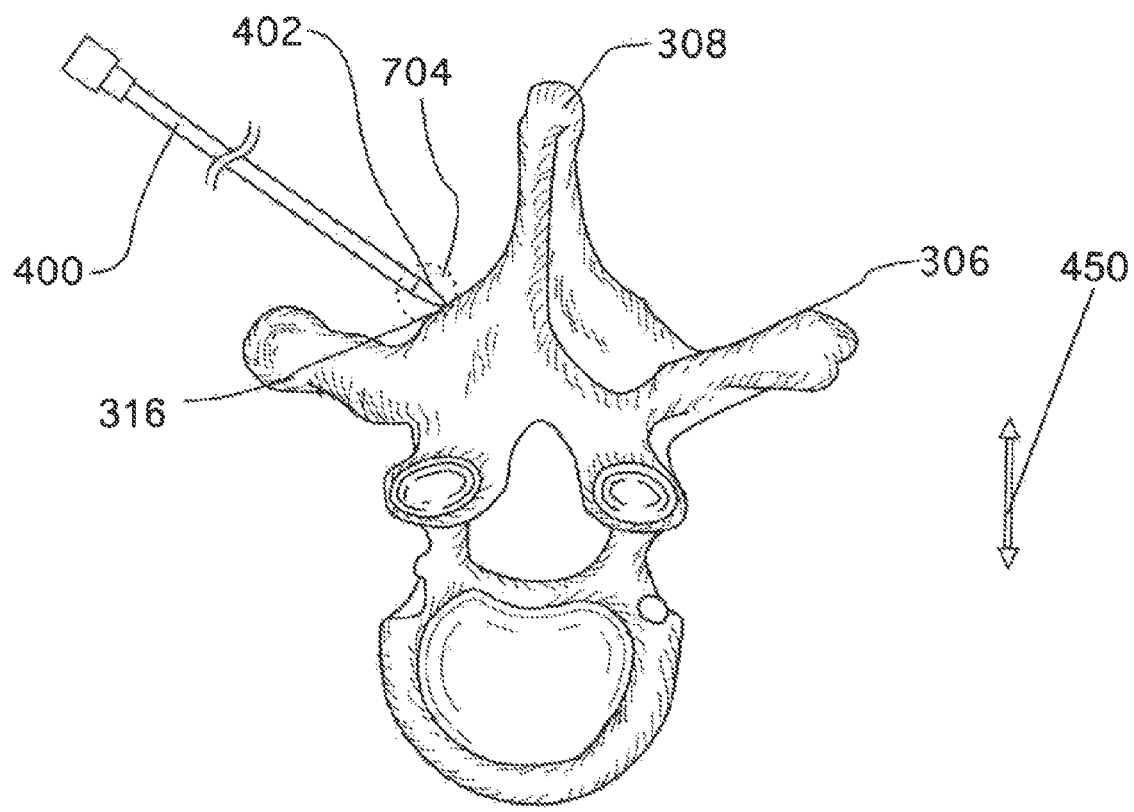
FIG. 7 illustrates an alternate position of an electrosurgical device with respect to the thoracic vertebrae in accordance with an embodiment of a method of the present invention.

In an alternate embodiment, the target site 310 may not be the superolateral aspect 318 of the transverse process and the region immediately superior thereto. Rather, the target site 310 may be the lamina 316 of the vertebra 300, as shown in FIG. 6, where the medial branch of the dorsal rami branches into the ascending and descending branches of the dorsal rami. Referring to FIG. 7, wherein a thoracic vertebra is shown from a cranial view looking along the coronal plane, in this embodiment, the electrosurgical device 400 may be inserted into the patient's body such that it is generally upstanding relative to the lamina 316 of the vertebra 300. In some embodiments an electrosurgical device may be positioned with the aid of an introducer apparatus as discussed previously. In order to position electrosurgical device 400 such that it is generally upstanding relative to the lamina 316 of the thoracic vertebra 300, electrosurgical device 400 may be angled such that it is oriented substantially away from an anterior-posterior (AP) axis 450 of the body, in a substantially lateral direction. In some embodiments, the electrosurgical device may be oriented at an angle of between about 15.degree. and about 65.degree. away from the AP axis in a substantially lateral direction. More specifically, electrosurgical device 400 may be oriented at an angle of about 45.degree. away from the AP axis, in a substantially lateral direction. Electrosurgical device 400 may then be inserted until it contacts the lamina 316. This embodiment may be useful in cases where the user is particularly concerned about causing pneumothorax in the patient. That is, since the electrosurgical device is directed at the lamina 316, and not towards the intertransverse space, there may be a decreased risk of accidentally puncturing the pleural sac of the patient.

In an alternate embodiment, a user may insert a second electrosurgical device into the patient's body. The second electrosurgical device may be inserted at the same vertebral level as the first electrosurgical device. In such an embodiment, the second electrosurgical device may be inserted in the same manner as described hereinabove with reference to FIG. 7; however, the second electrosurgical device may be inserted such that it is positioned at a distance from the first electrosurgical device. For example, the first electrosurgical device may be positioned as described above with reference to FIG. 7, and the second electrosurgical device may be positioned superior to the first electrosurgical device, at a distance of between about 0.1 cm to about 2 cm away from the first electrosurgical device. In some particular embodiments, the first and second electrosurgical devices are positioned about 1 cm apart from each other. In these embodiments, energy may be delivered in a bipolar manner, such that a lesion forms substantially between the first electrosurgical device and the second electrosurgical device.

The steps of inserting and positioning electrosurgical device 400 may optionally be followed, for example prior to the commencement of the step of delivering energy, by any number of steps, including, but not limited to, one or more of: measuring one or more properties of a device or of tissue at or near the target treatment site; applying a stimulation signal to a tissue (for example, neural tissue) at or near the target treatment site; measuring the reaction to stimulation (for example, the somato-sensory evoked potential, or SSEP) of a tissue (for example, muscular or neural tissue) in response to the application of a stimulation signal at or near the target treatment site; inserting or removing material at or near the target treatment site; and performing another treatment procedure at or near the target treatment site. Further details regarding these steps may be found in U.S. patent application Ser. No. 11/105,527 (filed on Apr. 14, 2005), Ser. No. 11/280,604 (filed on Nov. 15, 2005), Ser. No. 11/356,706 (filed on Feb. 17, 2006), Ser. No. 11/381,783 (filed on May 5, 2006), and Ser. No. 11/368,509 (filed on Mar. 7, 2006). Following the performance of one or more of the above optional steps, electrosurgical device 400 may be reinserted, moved, or otherwise repositioned and any optional steps may then be repeated.

In some embodiments, the step of delivering energy involves the creation of a lesion 404 at or adjacent to the superolateral aspect of the transverse process, or alternatively, the creation of a lesion 704 at the lamina of the vertebra. In any embodiments, as described hereinabove, the lesion may be created substantially distal to an energy delivery portion of the energy delivery device. Such lesions may be effective to alter a function of at least a portion of a medial branch of a dorsal ramus nerve. In some embodiments, the energy is delivered as radiofrequency electrical current having a frequency of between about 10 kHz and about 1000 kHz, at a power of about 50 W, may be delivered to the probe.

In embodiments of the present invention, the step of delivering energy to the tissue is preceded by, and/or performed at least partially concurrently with, a step of cooling the energy delivery portion of the electrosurgical device. As described hereinabove, in some embodiments, cooling may be achieved via the internal circulation of a fluid within electrosurgical device 400. In other embodiments, other means for cooling may be used, as described in U.S. patent application Ser. No. 11/457,697, previously incorporated herein by reference. Cooling may be used to reduce the temperature of the tissue in the vicinity of the site of energy delivery, allowing more energy to be delivered without causing an increase of temperature in surrounding tissue to an unsafe level. The delivery of more energy allows regions of tissue further away from the energy delivery portion to reach a temperature at which a lesion can form, thus increasing the maximum size/volume of the lesion. Furthermore, depending on the structure of the electrosurgical device, cooling may allow for a lesion to form at a position that is substantially distal to and, in some embodiments, spaced from the energy delivery portion. In some embodiments, again depending on the structure of the electrosurgical device, the lesion may from more in one direction than in another direction. For example, the lesion may form substantially distal to the energy delivery portion or may form substantially in another direction, depending on the structure of the electrosurgical device. Thus, cooling an electrosurgical probe may change the size, shape, and location of formation of a lesion. The lesion may be oblong or spherical in shape. In other embodiments the lesion may have a non-uniform shape.

In further embodiments, the step of cooling the electrosurgical device may be performed in a pulsed or intermittent manner. This may allow for a more accurate measurement of tissue temperature by a temperature sensing device associated with the electrosurgical device. For example, in embodiments wherein the electrosurgical device is cooled via the internal circulation of a cooling fluid delivered by a pump, the pump may be operated in a pulsed or intermittent manner. When the pump is 'on', fluid will circulate within the electrosurgical device, and the electrosurgical device and surrounding tissue will be cooled; when the pump is 'off', fluid will not circulate within the electrosurgical device, and heat from the tissue in the vicinity of the electrosurgical device may conduct back towards the electrosurgical device, causing the electrosurgical device to heat to a temperature that is more indicative of the temperature of the tissue in the vicinity of the electrosurgical device. The temperature sensing device may sense this temperature, and may thus give a more accurate reading of the temperature of the tissue in the vicinity of the electrosurgical device. When the pump returns to the 'on' position, the electrosurgical device will again be cooled, and the tissue adjacent the electrosurgical device will return to a cooler temperature. The pulsing of the pump may coincide with pulsing of energy delivered to the electrosurgical device, described further herein below, such that cooling is only supplied to the electrosurgical device while energy is being delivered.

In some embodiments, the active cooling of the electrode may be modulated during energy delivery (and in some cases, accompanied by a modulation of energy delivery), for example as follows: energy may be delivered initially in conjunction with cooling of the electrode so that a lesion begins to form at some distance distally spaced apart from the electrode; cooling may then be reduced, causing the lesion to extend at least partially in the direction of the electrode. Thus, a further feature of some embodiments of the present invention involves the control of cooling parameters in order to create a lesion at a desired location relative to the electrode. Further details regarding this feature are found in U.S. patent application Ser. No. 11/457,697, previously incorporated herein by reference. For example, an 18 AWG probe having an exposed distal tip about 1.5 mm to about 2 mm in length and being cooled by a cooling fluid having a temperature of less than 30 degrees Celsius at a rate of at least 10 mL/minute, will form a lesion about 1.5 mm distal to the electrode tip. As the cooling is decreased, for example by lowering the fluid flow rate, the lesion will form closer to the probe tip. The parameters of cooling may be adjusted before, during or after energy delivery.

In some embodiments wherein the degree of cooling is modified during the course of a treatment procedure, the amount or degree of cooling supplied to the electrosurgical device may be controlled actively by a user by modifying a flow-rate, or a temperature of the cooling fluid. For example, a temperature measured at the distal region of the electrosurgical device may be displayed on a screen or other display means. Based on this temperature, a user may desire to increase the amount of cooling supplied to the electrosurgical device, for example if the temperature is above a certain threshold level. The user may, in some embodiments, adjust the amount of cooling supplied by increasing the flow-rate of cooling fluid. This may be accomplished by turning a knob on a pump, for example, or by opening a valve. In other embodiments, the control of cooling may be passive and/or automatic. For example, a computer may automatically adjust a fluid flow-rate based on a temperature measured at the distal region of the electrosurgical device. In another example, a fluid flow-rate may be fixed during the course of a treatment procedure, and may not be modified.

In some embodiments, after the creation of a lesion, electrosurgical device 400 may be repositioned, and energy may again be delivered in order to form one or more further lesions. For example, after the formation of a first lesion, the electrosurgical device 400 may be withdrawn from the target site either partially or fully. In the case of partial withdrawal, energy may be delivered to the site at which the electrosurgical device 400 has been withdrawn to, such that a second lesion is formed. In the case of full withdrawal, electrosurgical device 400 may be re-inserted and re-positioned at a second location, and energy may be delivered to the second location to form a further lesion. The step of repositioning may be performed any number of times, to form any number of lesions, as determined by a user. In embodiments comprising a steerable electrosurgical device, the electrosurgical device may be repositioned without withdrawing the probe, by actuating the steering means associated with the probe.

In some embodiments, any or all of the method steps described above may be performed with the aid of imaging. For example, the step of inserting electrosurgical device 400 may be performed under X-ray fluoroscopic guidance. In a further embodiment, the imaging may be performed in a gun-barrel manner, wherein the device is visualized along its longitudinal axis.

In some embodiments, rather than being delivered in a continuous manner, energy may be delivered in a series of amplitude or frequency modulated pulses, whereby tissue heating is inhibited by interrupting periods of energy delivery with periods in which energy is delivered at a lower voltage. In one specific embodiment, energy is delivered according to a set duty cycle of signal on time/off time, wherein the signal is 'on' less than 100% of the time, as follows: during signal 'on time' energy is delivered at a voltage that may beneficially be higher than voltages that can safely be used during continuous energy delivery (100% duty cycle) procedures; during signal 'off time', the heat generated in the vicinity of the probe may disperse throughout the tissue, raising the temperature of tissue away from the probe, while tissue in the vicinity of the probe drops; energy is again applied and the delivery is cycled through 'on time' and 'off time' until a predetermined endpoint (e.g. time or temperature) is reached or until a practitioner decides to end the treatment. The reduction in temperature of tissue in the vicinity of the electrode during signal 'off time' may allow a higher voltage to be used (during 'on time'), than would tend to be used in a continuous energy delivery procedure. In this way, the pulsing of energy delivery, either between signal 'on time' and 'off time', as described above, or between a higher voltage and a lower voltage (for example, a voltage capable of generating a lesion in the tissue and a voltage not capable of generating a lesion in the tissue, given the frequency of energy being delivered), the total amount of current deposited into the tissue may be sufficient to create a larger lesion, at a further distance from the probe, than would be possible using continuous energy delivery without maintaining the tissue in the vicinity of the probe at a temperature that may cause charring. As mentioned hereinabove, the creation of a larger lesion is beneficial as it would require relatively less insertion and energy delivery steps in order to adequately treat the tissue.

Depending, for example, on the configuration and positioning of the electrosurgical device 400, as well as the degree of cooling supplied to the electrosurgical device 400, the lesion formed at the target site 310 may be of a variety of shapes and sizes. As described in U.S. patent application Ser. No. 11/457,697, previously incorporated herein by reference, lesion shape and location may be affected by the length of the energy delivery portion, for example an active electrode, of the electrosurgical device. The shorter the active electrode, the more distally, relative to the electrosurgical device, the lesion will form. In addition, the shape of the lesion will be generally more spherical if less of the active electrode is exposed. For example, if the exposed length of the distal end is limited substantially to the distal-most hemisphere, i.e. the face, of the tip, then a substantially spherical lesion may form primarily distally with respect to the electrosurgical device. Conversely, if more of the tip is exposed, then the lesion will appear more oblate and may form more radially (i.e. perpendicular to the longitudinal axis of the electrosurgical device) around the distal end and the component of the lesion distal to the distal end will decrease. Thus, depending on the size and shape of the active electrode of the electrosurgical device, the size and shape of the lesion may vary. For example, as shown in FIG. 4, in embodiments wherein the active electrode 402 of electrosurgical device 400 extends proximally along the length of the probe for a small distance, for example between about 2 mm and about 7 mm, and with a sufficient amount of cooling, for example between about 10 ml/min and about 25 ml/min, lesion 404 may form around the conductive portion as well as distal to the probe. Because lesions formed by this method may be substantially large, for example between about 100 mm$^3$ and about 1200 mm$^3$ in volume, this method may be particularly useful for lesioning of the nerves of the medial branch of the dorsal ramus at the thoracic region of the spine. In some embodiments the lesion formed may be greater than 1200 mm.sup.3.

Figure 10A:
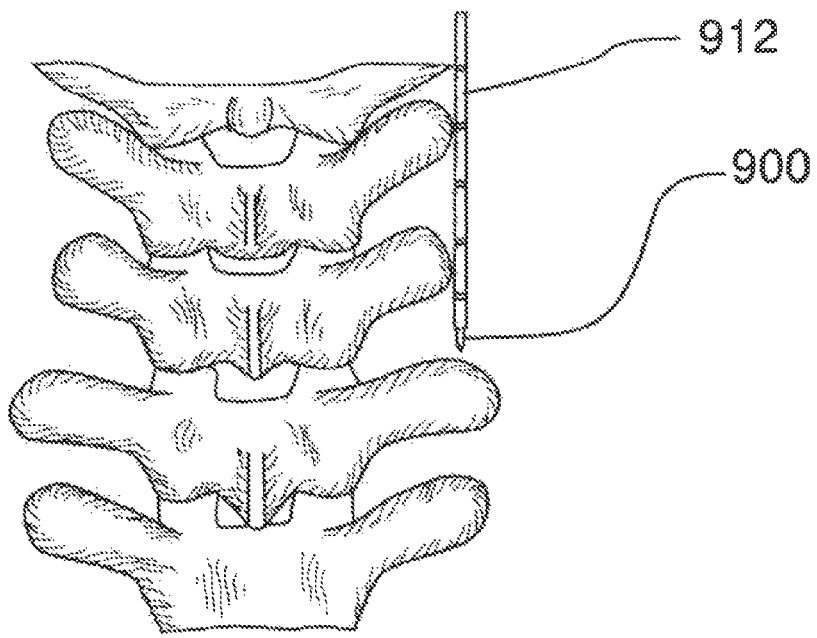
FIG. 10A shows an anterior-posterior view of an electrosurgical device at a vertebra in the upper thoracic portion in accordance with an embodiment of the present invention.
Figure 10B:
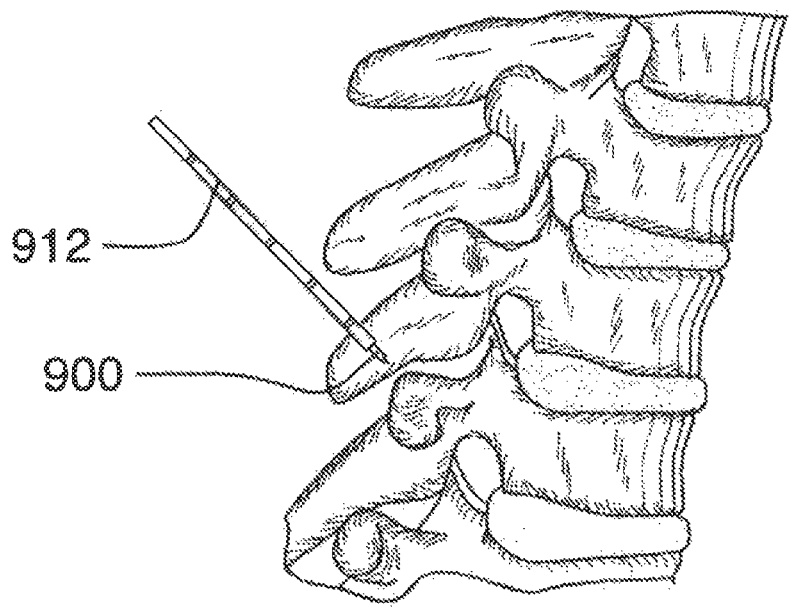
FIG. 10B shows a lateral view of an electrosurgical device at a vertebra in the upper thoracic portion in accordance with an embodiment of the present invention.
Figure 11A:
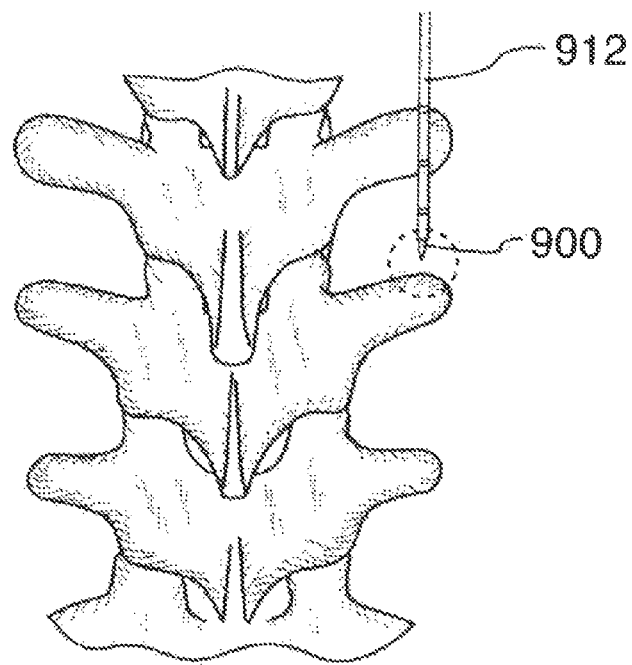
FIG. 11A shows an anterior-posterior view of an electrosurgical device at a vertebra in the mid-thoracic portion in accordance with an embodiment of the present invention.
Figure 11B:
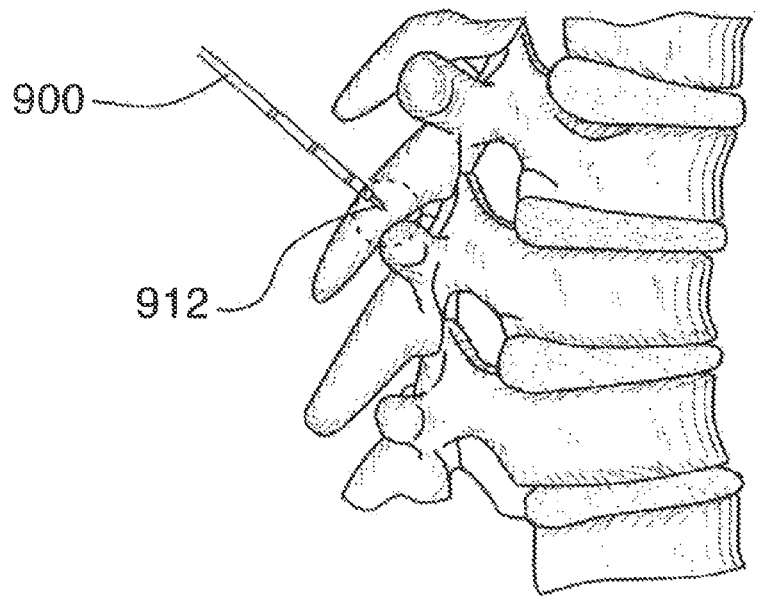
FIG. 11B shows a lateral view an electrosurgical device at a vertebra in the mid-thoracic portion in accordance with an embodiment of the present invention.
Figure 12A:
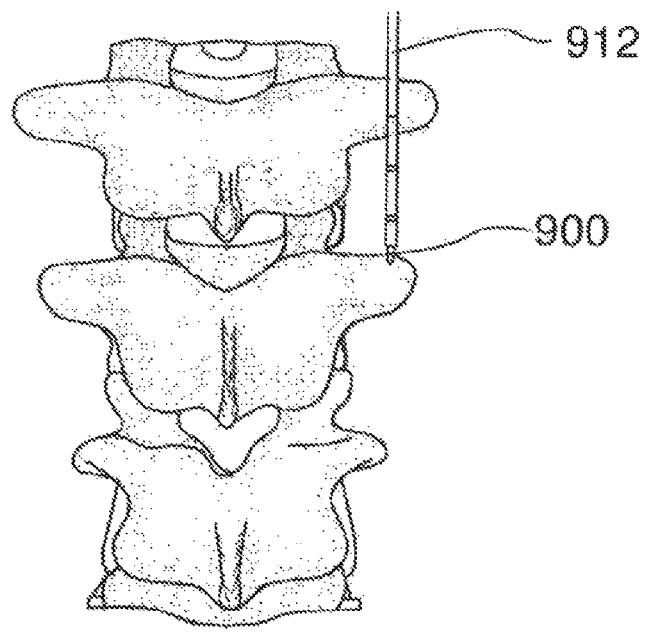
FIG. 12A shows an anterior-posterior view of an electrosurgical device at vertebra in the lower-thoracic portion in accordance with an embodiment of the present invention.
Figure 12B:
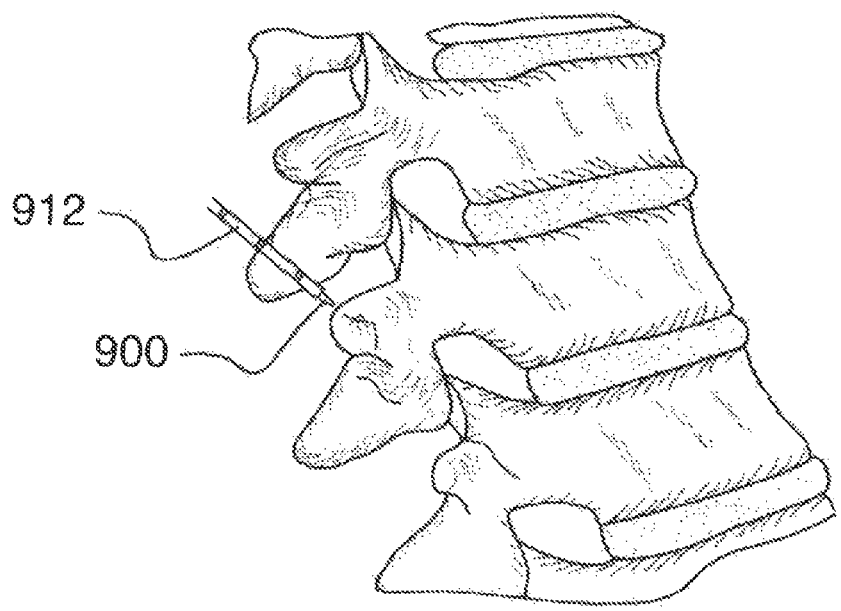
FIG. 12B shows a lateral view of an electrosurgical device at vertebra in the lower-thoracic portion in accordance with an embodiment of the present invention.
Figure 13B:
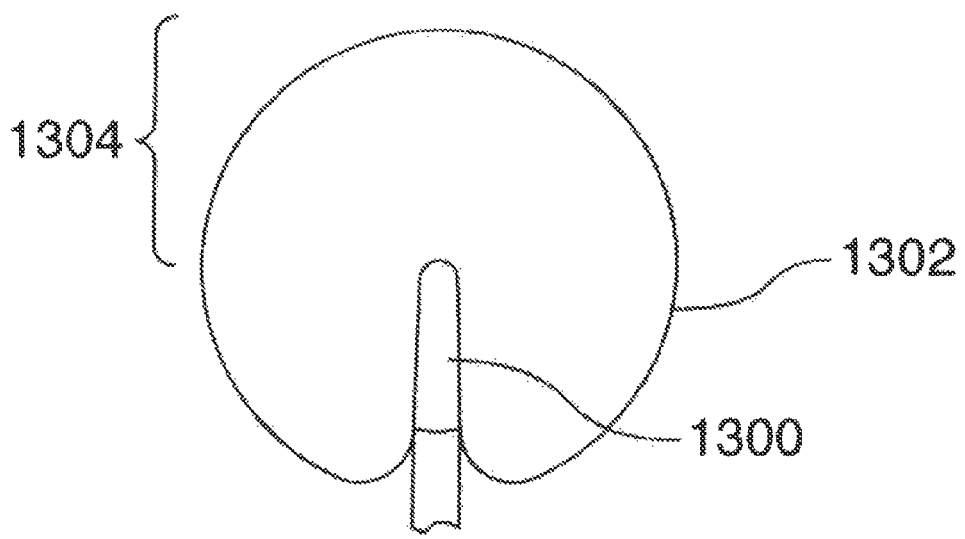
FIG. 13B shows a lesion in accordance with another embodiment of the present invention.
Figure 13A:
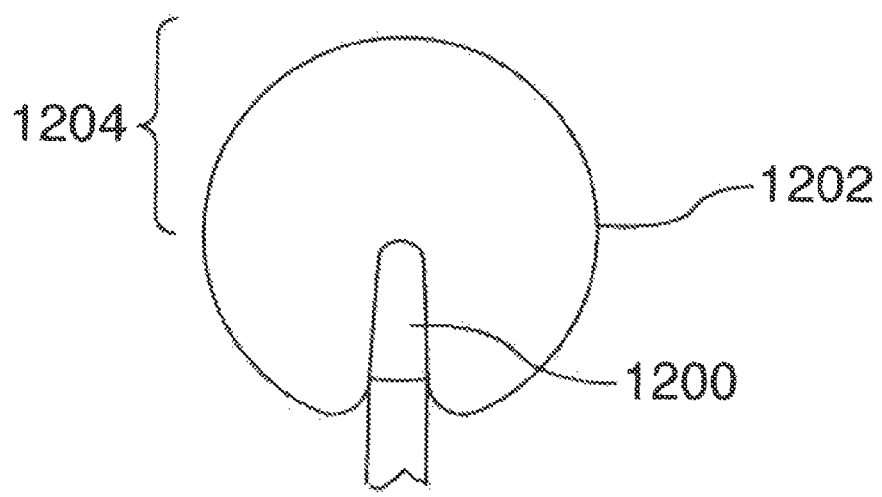
FIG. 13A shows a lesion in accordance with one embodiment of the present invention.

In accordance with the methods outlined in the present disclosure, the electrosurgical device or probe is positioned near the course of the target nerve. When energy is applied through the probe tip a lesion forms that blankets around the edges of the bone. In one embodiment the lesion is limited to the dorsal rami and the nerve root and the lateral branch of the dorsal root remain unaffected. In the upper and lower section of the thoracic spine from T1-T4 and T9-10, the medial branch of the dorsal ramus nerve crosses the superior-lateral portion of the transverse process and the variability decreases near the bone. Hence a smaller tip size is sufficient to create an effective lesion. In one embodiment as indicated in FIG. 12, the probe tip 1200 is about 3.5 mm and forms a lesion 1202 with a diameter of about 8 mm. The lesion 1202 forms substantially distal to the probe tip 1200. The lesion may form between the probe tip 1200 and a segment of the thoracic vertebra. In one example the segment of the thoracic vertebra is the transverse process. More specifically, the segment is the superior-lateral aspect of the transverse process. The distal projection 1204 of the lesion is about 4 mm from the probe tip with a lesion volume of about 270 mm$^3$. The distal projection is defined as the distance between the probe tip and the distal edge of the lesion. In alternate embodiments the lesion diameter can be about 6 mm to about 10 mm. In some embodiments the lesion diameter can be larger than 10 mm. In one example of embodiment of the present invention the electrosurgical device 900 is inserted at the T4 vertebral level as indicated in FIG. 10. In another example the device 900 is inserted at the T10 vertebral level as shown in FIG. 11

In the mid thoracic region from T5-T9, there is a greater variability in the path of the target nerve as the medial branch of the dorsal ramus cross through the intertransverse space. Hence, an electrosurgical device with a larger tip size is required in order to effectively lesion the target nerve. In one embodiment the probe tip 1300 is about 5 mm and lesion 1302 has a diameter of about 12 mm. The lesion 1300 forms substantially distal to the probe tip 1300. The lesion may form between the probe tip 1300 and a segment of the thoracic vertebra. In one example the segment of the thoracic vertebra is the transverse process. More specifically the segment is the superior-lateral aspect of the transverse process. The distal projection 1304 is about 5 mm from the probe tip with a lesion volume of about 900 mm$^3$. In another example of the present embodiment the lesion size may vary from about 8 mm to about 16 mm. In some embodiments the lesion size may be greater than 16 mm in diameter. In one example of embodiment of the present invention the electrosurgical device 900 is inserted at the T6 vertebral level as shown in FIG. 11.

Thus, embodiments of the present invention allow for the treatment of a thoracic region of a patient's body. Particularly, methods of the present invention may be used to create a lesion at a medial branch of a thoracic dorsal ramus, for example in order to treat pain or other pathologies involving the medial branch.

As described hereinabove, embodiments of a method of the present invention allow for the creation of a lesion between an energy delivery portion of an electrosurgical device and some predetermined location, such as a segment of a thoracic vertebra. For example, a lesion may be created substantially distal to the energy delivery portion by delivering energy to the energy delivery portion and cooling the energy delivery portion. This provides an advantageous benefit not found in the prior art, in that it obviates the need for a probe to be placed in very close proximity to a target nerve in order to effectively lesion the target nerve Some embodiments of the method comprise positioning an energy delivery portion of an electrosurgical device to face a segment of a thoracic vertebra at a distance from the segment; and cooling the energy delivery portion and delivering energy through the energy delivery portion. In some embodiments a lesion is formed at least substantially distal to the energy delivery portion. In some embodiments the lesion is formed at a location at least between the energy delivery portion and the segment of the thoracic vertebra.

In some particular embodiments, the electrosurgical device may be inserted and positioned in a manner that is relatively safe, effective, and efficient. In addition, embodiments of the present invention allow for the creation of a relatively larger lesion than previously possible, thereby reducing the amount of lesions that must be created in order to sufficiently treat the patient.

Embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating a thoracic region of a patient's spine, the method comprising:
   inserting a first electrosurgical device at a segment of a transverse process of a first thoracic vertebra;
   moving the first electrosurgical device in a cranial direction until a distal tip of the first electrosurgical device slips over a superolateral aspect of the transverse process;
   inserting a second electrosurgical device at a segment of a second thoracic vertebra adjacent to the first thoracic vertebra;
   moving the second electrosurgical device in a caudal direction until a distal tip of the second electrosurgical device slips over a inferiolateral aspect of the transverse process; and
   delivering energy between the first electrosurgical device and the second electrosurgical device in a bipolar manner while cooling the first electrosurgical device and the second electrosurgical device.

2. The method of claim 1, wherein the cooling and the delivering energy cooperate to form a lesion between the first electrosurgical device and the second electrosurgical device.

3. The method of claim 1, wherein the superolateral aspect of the transverse process of the thoracic vertebra comprises a centroid region of a transverse process.

4. A method of treating a nerve in the thoracic region of a patient's body, the method comprising:
   positioning a first energy delivery portion of a electrosurgical device so as to face a region where the nerve is likely to be found, at a distance from the region, the region being located distal to the first energy delivery portion and containing a transverse process of a first thoracic vertebra; and
   moving the first energy delivery portion in a cranial direction until a distal tip of the first energy delivery portion slips over a superolateral aspect of the transverse process;
   positioning a second energy delivery portion of the electrosurgical device at a segment of the region adjacent to the nerve;
   moving the second energy delivery portion in a caudal direction until a distal tip of the second energy delivery portion slips over a inferiolateral aspect of the transverse process;
   cooling the first and second energy delivery portions of the electrosurgical device and delivering energy from the first and second energy delivery portions to form a lesion at the nerve.

5. The method of claim 4, wherein the cooling and the delivering energy cooperate to form a lesion at a location at least between the first and second energy delivery portions and the superolateral aspect of the transverse process of the thoracic vertebra.

6. The method of claim 4, wherein the distance between the first and second energy delivery portions and the region is 0.5 mm to 4 mm, respectively.

7. The method of claim 4, wherein the nerve innervates a thoracic facet joint of the patient's body.

8. The method of claim 4, wherein the nerve comprises a medial branch of a thoracic dorsal ramus nerve of the patient's body.

9. The method of claim 4, wherein the first and second energy delivery portions are positioned at a location in the region bounded by:
   a superior margin of the transverse process,
   an inferior margin of a superjacent transverse process,
   an anterior margin of the transverse process and an anterior margin of the superjacent transverse process,
   a posterior margin of a spinous process of the thoracic vertebra,
   an inferior articular process of the thoracic vertebra and a superior articular process of a superjacent thoracic vertebra, and
   a lateral margin of the transverse process and a lateral margin of the superjacent transverse process.

* * * * *